(12) United States Patent
Srinivasan

(10) Patent No.: US 8,412,539 B2
(45) Date of Patent: Apr. 2, 2013

(54) HANDHELD MEDICAL INFORMATION MANAGEMENT DEVICE

(76) Inventor: Rajagopal Srinivasan, Pittsburgh, PA (US)

( * ) Notice: Subject to any disclaimer, the term of this patent is extended or adjusted under 35 U.S.C. 154(b) by 238 days.

(21) Appl. No.: 12/757,656

(22) Filed: Apr. 9, 2010

(65) Prior Publication Data

US 2010/0286997 A1     Nov. 11, 2010

Related U.S. Application Data

(60) Provisional application No. 61/212,146, filed on Apr. 9, 2009.

(51) Int. Cl.
  *G06Q 10/00*   (2012.01)
  *G06Q 50/00*   (2012.01)
  *H04M 11/00*   (2006.01)
(52) U.S. Cl. .............................. 705/2; 705/3; 379/90.01
(58) Field of Classification Search .................. 705/2–3; 379/90.01
  See application file for complete search history.

(56) References Cited

U.S. PATENT DOCUMENTS

| | | | |
|---|---|---|---|
| 5,319,543 | A | 6/1994 | Wilhelm |
| 6,874,085 | B1 | 3/2005 | Koo et al. |
| 7,039,628 | B2 | 5/2006 | Logan, Jr. |
| 7,542,911 | B2 | 6/2009 | Barret et al. |
| 7,630,908 | B1 | 12/2009 | Amrien et al. |
| 2002/0188953 | A1 | 12/2002 | Kenworthy |
| 2003/0115447 | A1 | 6/2003 | Pham et al. |
| 2003/0165128 | A1 | 9/2003 | Sisodia et al. |
| 2003/0179223 | A1 | 9/2003 | Ying et al. |
| 2004/0068421 | A1 | 4/2004 | Drapeau et al. |
| 2004/0193449 | A1 | 9/2004 | Wildman et al. |
| 2004/0260577 | A1 | 12/2004 | Dahlin et al. |
| 2005/0035862 | A1 | 2/2005 | Wildman et al. |
| 2005/0063420 | A1 | 3/2005 | Graves |
| 2005/0086079 | A1 | 4/2005 | Graves et al. |
| 2005/0272275 | A1 | 12/2005 | Graves |
| 2006/0282459 | A1 | 12/2006 | Kabala |
| 2007/0273517 | A1 | 11/2007 | Govind |
| 2008/0194918 | A1* | 8/2008 | Kulik et al. ................... 600/300 |
| 2009/0234675 | A1 | 9/2009 | Irakam |
| 2009/0248437 | A1 | 10/2009 | Gucciardi et al. |
| 2012/0088481 | A1* | 4/2012 | Postma et al. ................. 455/417 |
| 2012/0119890 | A1* | 5/2012 | Collins et al. ............ 340/286.07 |

* cited by examiner

*Primary Examiner* — Luke Gilligan
(74) *Attorney, Agent, or Firm* — The Webb Law Firm

(57) ABSTRACT

A portable handheld medical information management device that includes a storage memory, a processor, an input device, a transceiver, a display, and software. The software includes programming instructions executable by said processor operative to communicate to a server over a network, said communication comprising sending messages to the server and receiving messages. The device can generate patient information screens on the display, using patient information from at least one received message from the server. The server can control the transceiver to interrogate proximate location devices and calculate a position based on location of proximate location devices. The device, in conjunction with the network and server, can route phone calls and other message-based communication over a local area network (LAN) enabling advanced logistic features such as reliable communication of critical messages; it can also interface effectively with traditional hospital extension based phone systems and the public phone network.

7 Claims, 17 Drawing Sheets

HANDHELD MEDICAL INFORMATION MANAGEMENT DEVICE

CROSS REFERENCE TO RELATED APPLICATIONS

This application claims the benefit of U.S. Provisional Patent Application Ser. No. 61/212,146, filed Apr. 9, 2009.

FIELD OF THE INVENTION

The present invention relates generally to a hospital medical communication system for improving emergent communications and information access between staff, physicians, and external medical persons.

BACKGROUND OF THE INVENTION

The demand for emergency care has risen from 90 million patient visits in 1997 to 120 million in 2007. Much attention has been paid to the shortage of qualified Emergency Physicians (EP), yet little attention has been paid to EP productivity, measured in patients per hour (pph), which has remained constant for the past 30 years.

Information plays a key role in modern medicine. Physicians and nurses depend on quick and reliable access to key information such as vital signs and lab results. The current systems used by the Emergency Department (ED) include paper charting or "health information technology" (HIT). These systems require physicians and nurses to waste time and effort searching for information or copying information from one system to another, introducing errors and fatal inconsistencies along the way.

Waiting times have consistently increased over the past decade, in particular the wait time before a patient is evaluated by a physician (so-called "door-to-physician time"). Although the total cost to society is difficult to quantify, a recent lawsuit involving the unexpected death of a celebrity's brother several hours after checking into an ED illustrates this point; delays in the ED are associated with increased death, disability, and litigation.

A competent EP can typically process 2-3 pph during a shift that typically lasts 8-12 hours, sometimes up to 24 hours. This rate has remained constant over the past 30 years. This bottleneck is so universal that some cannot fathom an EP seeing more than 2.5 pph safely. Currently available HIT has not consistently decreased door-to-physician time. In fact, many early adopters of ED HIT, such as paperless charting systems and Computerized Physician Order Entry (CPOE), have sustained decreases in physician throughput. Much HIT currently deployed in EDs not only impedes workflow, but also increases error rate and endangers patient safety. Finally, the statistics released in support of expensive HIT are rarely from controlled or blinded studies designed to prove benefit, but rather from anecdotal materials designed to market a product.

Communication of urgent information between physicians and nurses quickly becomes a logistic problem, and many EDs in the United States provide extension-based cordless phones to their employees for use during shifts. These phones clip onto scrub pants or fit into labcaot pockets; they are often called "pickle phones" due to their distinctive shape. Each phone costs $500-$800, and provides extremely limited functionality (caller ID, call hold, rudimentary text messaging, dial-by-number, minimal data integration or entry).

SUMMARY OF THE INVENTION

The present invention provides a portable handheld medical information management device for rapid and targeted delivery of communication and information in a hospital setting. The portable medical information management device includes a number of subsystems implemented on the storage memory, processor, input device, transceiver, display, and software. The software formed by programming instructions executable by the processor are operative to run the subsystems. The handheld device can communicate to a server or network. The communication between the server and the handheld device includes messages to the server from the handheld device and received messages from the server. The handheld device having a virtual telephone having a virtual number stores a database of numbers corresponding to other devices authenticated on the network. This database may be stored on the handheld device or stored and updated on a server which can be queried as needed over a network. The telephone is operable to send and receive calls over the network. The device further includes capability to authenticate the user of the handheld device to a server by sending a message, the message creates a session between the server and the handheld device and the session continues until messages between the handheld device and the server are no longer present. These messages are sent and received between the server and device periodically. The device further includes a location module whereby the device can control the transceiver to interrogate proximate location devices and calculate a position based on location of these proximate location devices.

The portable handheld medical information management device also includes a display for showing patient information screens. By using the patient information from at least one received message from a server, the handheld device can show the physician information concerning a patient from the server database. In order to show information restricted by the size limitation of the handheld device, it is further operative to connect to a docking station attached to a host computer, whereby the authenticated session on the device is then transferred to the host computer and the patient information screens can be displayed on the host computer. The handheld device is further operative to interface to a server coupled to databases. The databases can include any hospital databases, patient information, electronic health record systems, electronic medical record systems, telephone directory database, private branch exchange (PBX) databases, public switched telephone network (PSTN) databases, and authentication service systems. In addition, more than one server can be used by the device to get information. During authentication, messages are passed between the server and handheld device. These messages can include authentication messages having user credentials in the form of a personal identification number (PIN), a login name, a password, an image, fingerprint, or retina scan can be used. The authentication includes an exchange of a plurality of messages between the handheld device and the server. The virtual telephone of the handheld device can place calls on a network, including the intranet, Internet, or the PSTN. The phone number assigned to the handheld device is received and configured by the device during the authentication process. When authentication is completed, external phones can connect to the virtual telephone device by the virtual number assignment. External phone calls include phones on the external public switched telephone network, including callers that have previously received the phone number via phone calls received and stored on their caller ID using a redial function on their telephone. The virtual number for the device can be assigned from a virtual number pool given to the server by a PBX. The virtual number is then assigned by the server to a user or device. Virtual number assignments can last for one session or multiple sessions.

In addition to telephone calls, the handheld device is also configured to send text messages to other devices on the network. The messages are in the form of critical messages because physicians and other users must respond by acknowledging that they have read the message. If an acknowledgement is not received in a pre-defined period of time, an alarm is activated on the device where the message has been received. In addition, a message on the sender's handheld device can be flagged or an alarm can be activated alerting the sender that the message has not been acknowledged. Critical messages can include text, images, or voice data. The software of the handheld device further includes programming instructions that can disable a user authenticated session if the handheld device has not been used for a length or duration of inactivity. When the handheld device has been deactivated, removal of all messages and patient records is automatic, and an alert is sent to the server that the handheld device is inactive. The inactive device is useless to a hacker. The handheld device can then be reactivated or re-authenticated during a disabled user session by the user by entering a PIN. The PIN can bypass authentication and is an expedited authentication technique.

In an exchange plurality of messages between the device and a plurality of servers, a request for identification of a proximate location device is included. Once the handheld device has been queried, the device can interrogate identification information from a proximate location device. The received information is used for matching said machine name to a machine name map in a database. The database can be stored on the handheld device or on the server. Interrogation of multiple handheld devices can also be accounted for and multiple map addresses can be used to calculate locations. The interrogation of location devices can be set to be periodic so that a running tally of the location of the device is always known. Updates of the location can occur on a set time interval or they can be triggered by a received message. The received message can come from a server or directly from a second handheld device. In addition, the received message can be received indirectly by a second handheld device via a server.

The transceiver of the present handheld device can communicate wirelessly via a secure encrypted wireless local area network (LAN). The LAN can run on the 802.11 G, 802.11B, 802.11A, and 802.11N protocols. The handheld device can include a bar code scanner. The display of the device can be touch sensitive and the device can include a camera or scanner for capturing images.

In accordance with another broad aspect, the present invention seeks to provide a medical information management system comprising a portable handheld device, a computer network, a handheld telephone number database, a server, and a number of location-specific devices. The server can be coupled to a database. The portable handheld device can be one in accordance with the previously described portable handheld device including storage memory, a processor, an input interface, a transceiver, software instructions, and a display. The computer network is accessible by both the server and the portable handheld devices. Over the computer network, authentication takes place between a user and a server. The user activates the portable handheld device, inputs their password information, and in response, to the activation, the server sends a message to create a session between the server and the handheld device. The session continues until interrupted or the user exits. The handheld telephone number database is a database that stores assigned numbers. The stored assigned numbers indicate the numbers of authenticated devices on the network. Each number is assigned and can be used to call specific handheld devices. The location-specific devices include a wireless transmitter operable to wirelessly transmit data signals including device identification codes to a transceiver of a handheld device.

The present invention further provides an information management system further comprising software to generate patient information screens on the display of the handheld device the patient information received from the server. The system can further include a docking station which is attached to a host computer. The docking station is operable to couple with a portable handheld device. When coupled, the portable handheld device can transfer a session to the host computer and patient information screens or other information can be displayed on the host computer. The handheld device of the system can interrogate the location-specific device and calculate the position based on the location of the proximate device. When the handheld device interrogates the location-specific device, the information can be displayed as a map on the patient information screens.

In accordance with another broad aspect of the invention, the present invention seeks to provide a computer implemented method of getting emergent care to patients using a portable medical information management system. The method provides for having a portable handheld device, a computer network, and a server. A session is created between the server and handheld device such that the session is configured to continue communicating messages to the handheld device unless interrupted. The handheld device is a locating device, by sending a location request to the server. Transmission of data by the server to the transceiver of a second medical worker's handheld device can activate the second handheld device to interrogate the location-specific device for device identification code. Calculations based upon the identification code can determine the proximate location of the second handheld device. A telephone is configured on the handheld device, including stored database of virtual telephone numbers to which calls can be completed. A server can be used to enter data from multiple databases. The data can be downloaded onto the handheld device or notification can be sent to the handheld device that data is awaiting download.

In accordance with another broad aspect of the present invention, the present invention seeks to provide a hospital personnel communication method whereby personnel can rapidly locate and communicate with other personnel in the hospital. The method includes the step of providing hospital personnel with a small, durable, portable handheld device in accordance with the present invention; authenticating the handheld device; assigning the portable handheld device with a private branch exchange (PBX) extension number; linking the PBX extension with hospital personnel; storing the PBX extension number, the hospital personnel's name and a device identifier on the server database; downloading the database to a portable handheld device; identifying location of hospital personnel comprising interrogating the proximate location of the handheld device and storing location on the database. The method further includes displaying the database of virtual numbers on the portable handheld device. When the database is displayed, a selection of a name or number from the database can be made and hospital personnel can be linked to PBX extensions from the display. The method also includes docking the portable handheld device at a docking station, showing information on a screen at the docking station. The docking station can override a patient entertainment center. The patient entertainment center can be a television or video broadcast from a remote location and/or running help screens or training information. The method further comprises generating patient information screens on the handheld device display and using the patient information from at least one received message from the server; connecting the handheld device to the docking station attached to the host computer whereby the session is transferred to the host computer; processing to show patient information screens on the display of the handheld device as well as additional patient information screens (such as X-rays too big to fit onto handheld display) on displays connected to the docking station host computer using patient information from at least one received message from the server.

BRIEF DESCRIPTION OF THE DRAWING(S)

DETAILED DESCRIPTION OF THE INVENTION

Figure 1A:
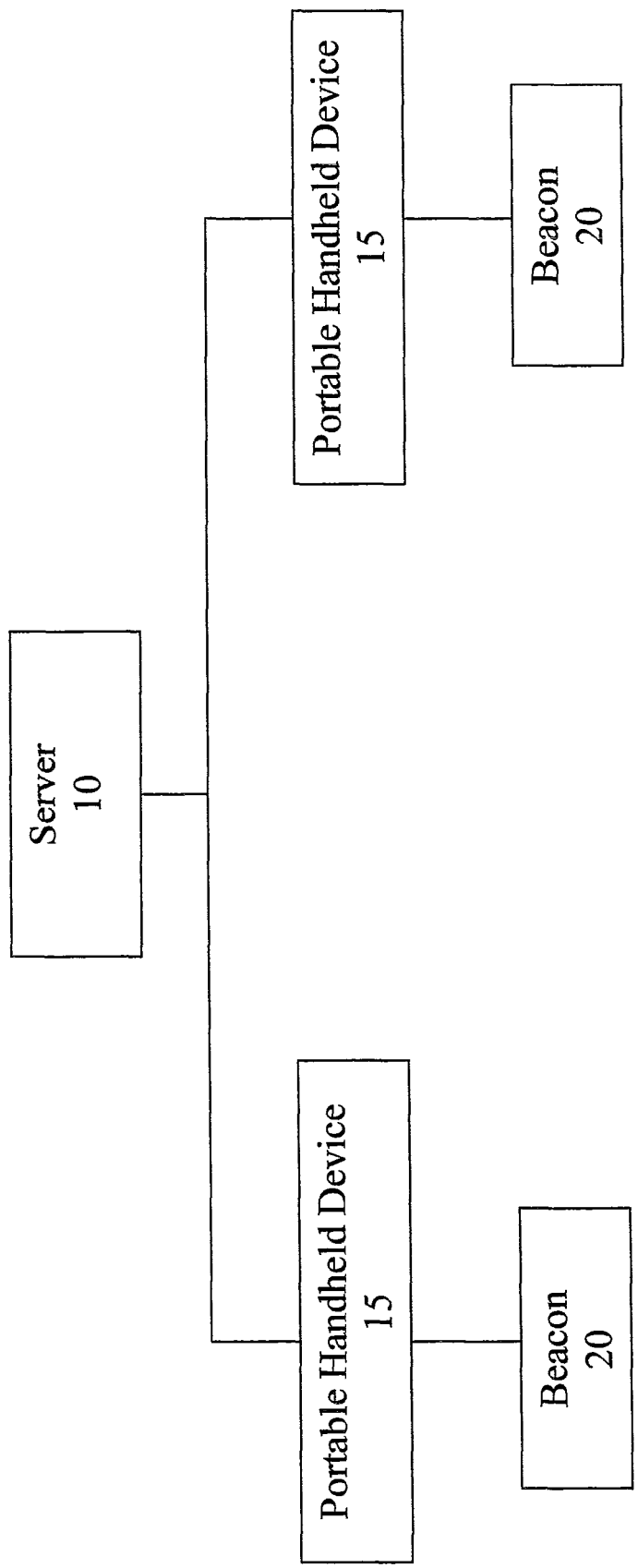
FIG. 1a is a block diagram showing a hardware configuration according to one embodiment of the present invention.

FIG. 1a shows one possible hardware configuration for a system according to the present invention. Portable handheld devices 15 are attached to data server 10. Data server 10 passes information to the proper portable handheld devices 15. A location beacon 20 can be proximate to one portable handheld devices 15. Portable handheld devices 15 are attached to Data server 10 via a hospital emergency department local area network (LAN) 5. For this configuration, one portable handheld device 15 might be in a nurse's hand, while the other portable handheld device 15 might be in a doctor's hand. The server 10 can be configured to transmit VoIP from one device 15 to another. This configuration might be used for an entire emergency department or hospital to enable communication between physicians and to facilitate locating important hospital personnel. Each portable handheld device 15 is assigned a network address. Each network address is stored on the data server in a telephone directory database together with the name of the person who was assigned the particular portable handheld device. The portable handheld device 15 receives a list of each network address or phone number for each portable handheld device 15 together with a name associated with that network address or portable handheld device 15. When a user activates a telephone dialing on the portable handheld device 15, the directory lists the names of each person who was assigned a portable handheld device 15 and optionally the telephone number or network address. It can also list telephone numbers that are assigned to non-portable handheld devices, such as hospital departments or desk telephones. Those of skill in the art will recognize that numerous other hardware configurations for the system of the present invention are possible.

Figure 1B:
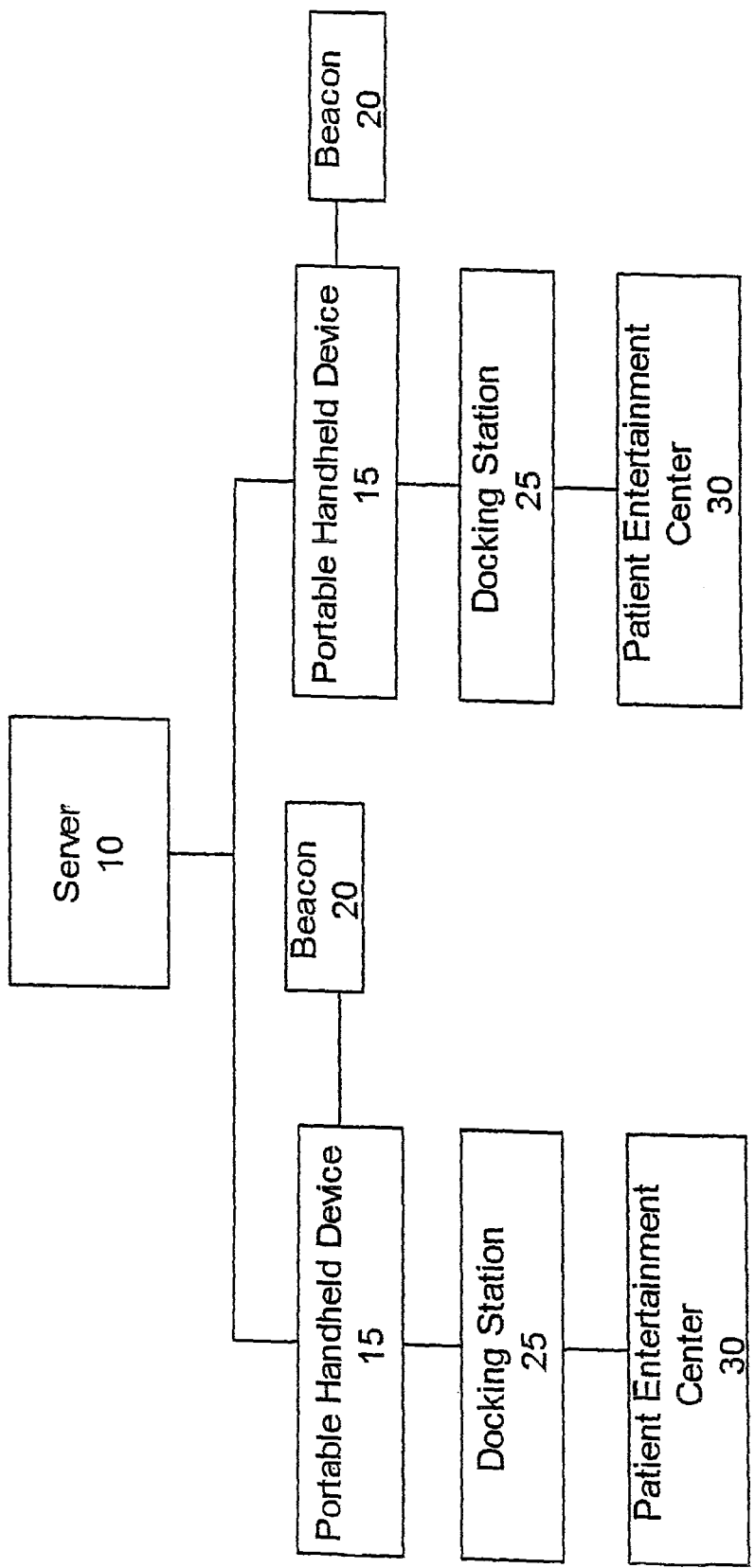
FIG. 1b is a block diagram showing a hardware configuration according to one embodiment of the present invention.

FIG. 1b shows another possible hardware configuration. Portable handheld devices 15 are attached to data server 10. A location beacon 20 can be proximate to one portable handheld device 15. Portable handheld devices 15 are also coupled to a docking station 25. Each of docking stations 25 may have direct access to data on server 10, or indirect access to data on server 10 via portable handheld device 15. A patient entertainment center 30, and optical scanner (not shown, which preferably includes a bar code reading capability) may each be attached to one of docking stations 25. This configuration might be used for an entire emergency department or hospital to enable display of information from the handheld devices 15 to the patient entertainment center 30 to facilitate patient interaction. Those of skill in the art will recognize that numerous other hardware configurations for the system of the present invention are possible.

Figure 1C:
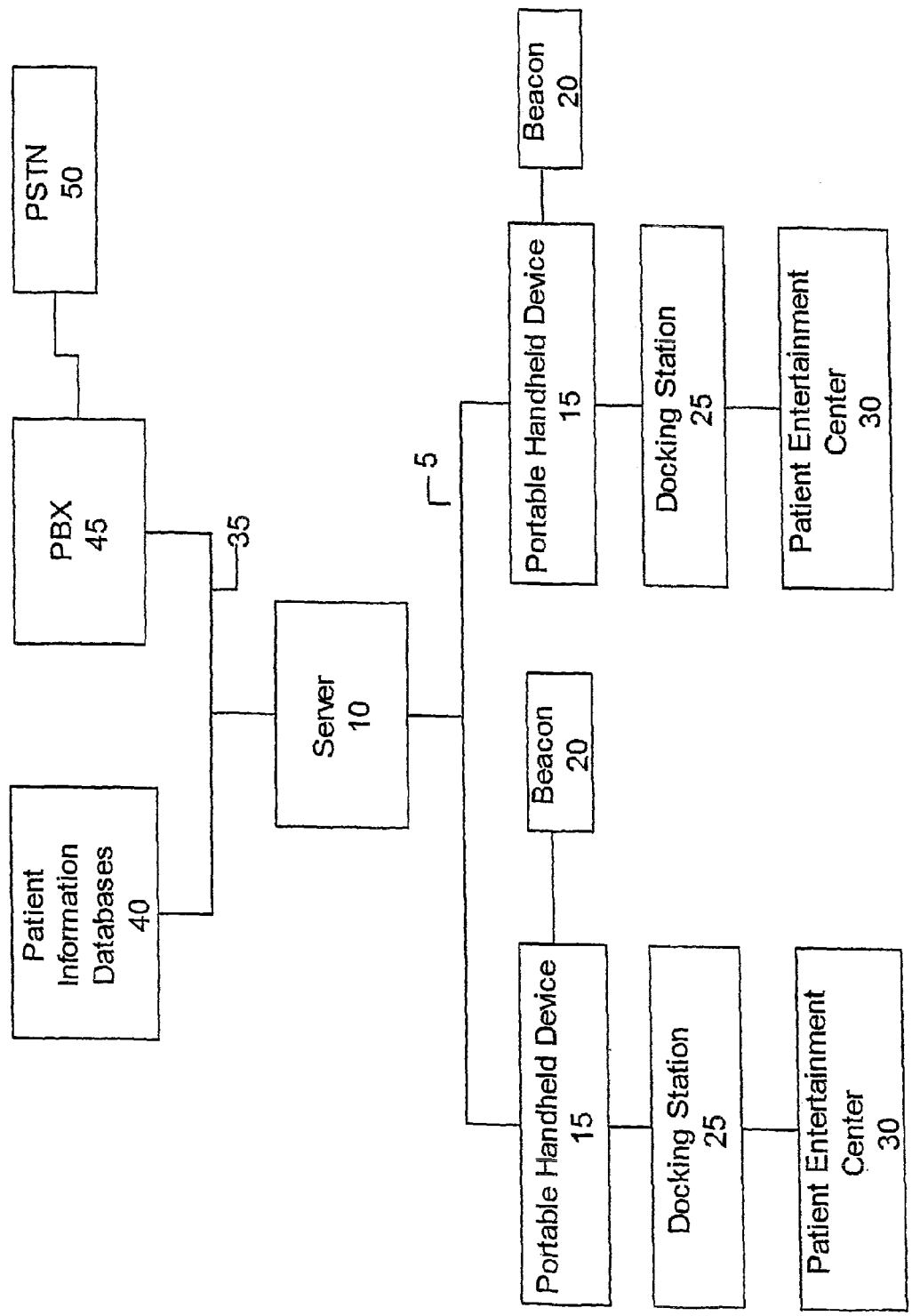
FIG. 1c is a block diagram showing a hardware configuration according to one embodiment of the present invention.

FIG. 1c shows another possible hardware configuration. Portable handheld devices 15 are attached to data server 10, communicating over ED network 5. Location beacons 20 can be proximate to portable handheld devices 15. Portable handheld devices 15 are also coupled to a docking station 25. Each of docking stations 25 may have patient entertainment centers 30. Data server 10 is attached to patient information databases 40 via local area network (LAN) 35. PBX 45 is also attached to data server 10 via LAN 35, and PSTN 50 is attached to PBX 45. Each of portable handheld devices 15 may have access to data on patient information databases 40 through server 10, or access to PSTN 50 via PBX 45 and server 10. The patient information databases could include information such as name, age, emergency contacts, release acknowledgements, and room-location of patients. The patient information could further include medical information such as x-rays, MRI, lab reports, medical history. Still further, the patient information databases 40 could include scheduled procedures, and current medications and next scheduled dosage. This configuration might be used for an entire emergency department or hospital for communicating internal or external. Those of skill in the art will recognize that numerous other hardware configurations for the system of the present invention are possible.

Figure 1D:
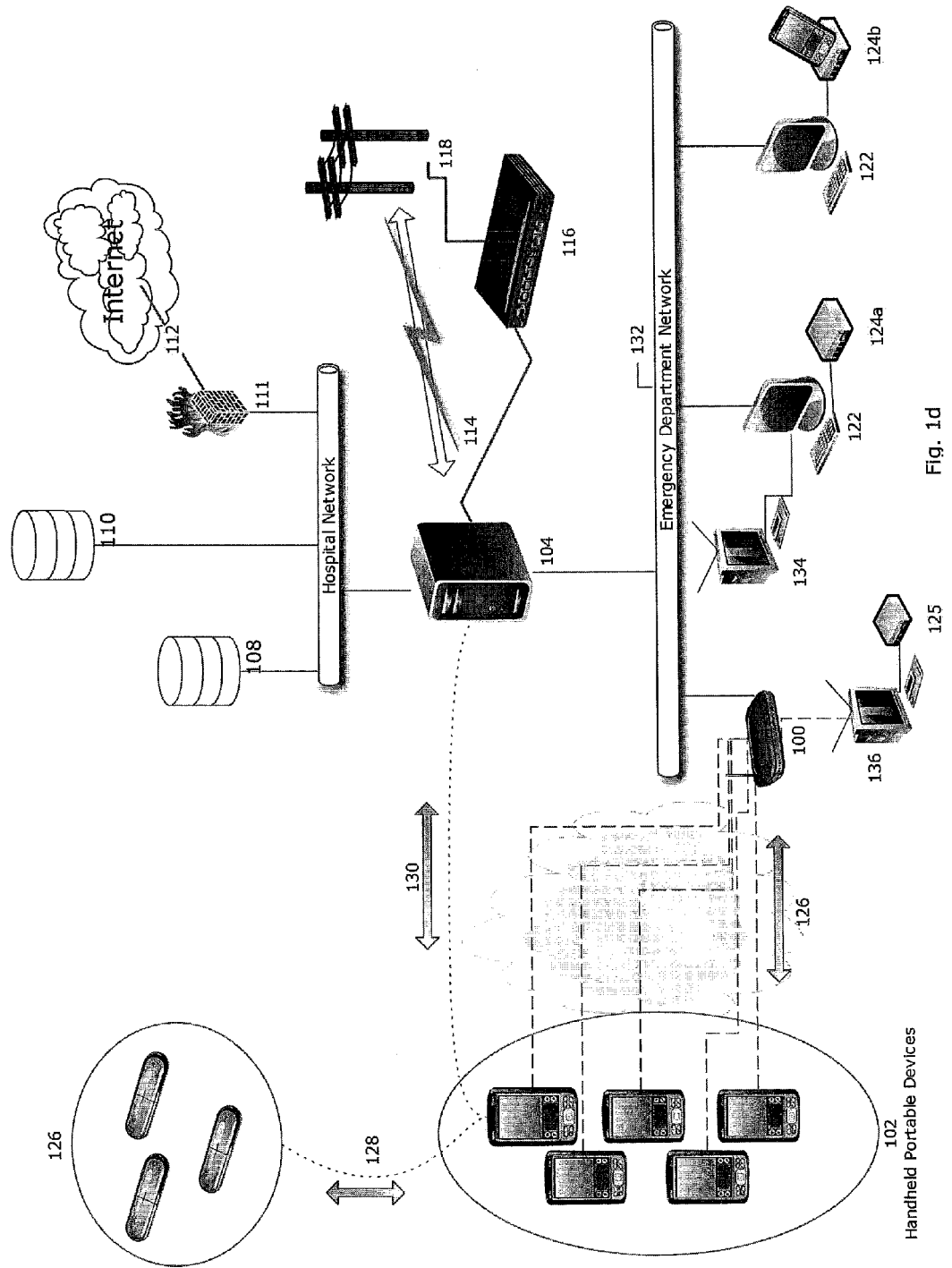
FIG. 1d is a schematic diagram showing a hardware configuration according one embodiment of the present invention.

FIG. 1d shows one possible hardware configuration for a medical information management system according to the present invention. The medical information management system is of particular use in a hospital environment that provides communication in an emergency department (ED). In the ED is a wireless access point 100 that connects a plurality of portable handheld devices 102 to an emergency department network 132 which is coupled to a logistic medical intelligence server (LMIS) 104 located in the hospital or offsite via a high-speed data link.

The LMIS 104 can provide access to information stored on a hospital network 106, including databases for emergency medical records 108 and medical information systems 110. LMIS 104 can also be connected via a communications channel and firewall 111 to the Internet 112. As is also shown in FIG. 1d, the LMIS 104 can be connected via a communication channel 114 to a hospital private branch exchange (PBX) 116. The PBX 116 provides telephony switching for telephony signals originating from and destined for a plurality of extension-based telephones (not shown) communicatively coupled to the PBX 116. The PBX 116 can assign one or more logical extensions to the LMIS 114, which allows internal or external telephone calls to be routed to the LMIS 114. The hospital PBX 116 is connected to the public switched telephone network (PSTN) 118, to permit messages from portable handheld devices 102 routed by the LMIS 104 to communicate with users of conventional telephone systems or plain old telephone systems (POTS).

In accordance with the present invention, LMIS 114 of the medical information management system supports sessions between the plurality of portable handheld devices 102 which allow medical staff to gain access to the communication networks 114 and records stored in the hospital network 106. Communications both to and from the plurality of portable handheld devices 102 are handled by LMIS 114, for example, voice messages in the form of voice-over IP can be routed to the hospital PBX 116 for outbound calls to the PSTN 118 or routed by the LMIS 14 to another handheld device 102.

LMIS 104 is also coupled to an emergency department network 120 having a plurality of dedicated docking workstation 122 connected thereto with ports for handheld devices 124a and 124b, and patient entertainment stations, 134 and 136, respectively. Patient entertainment stations 134 and 136 can be television sets receiving a television signal from a dedicated docking workstation coupled thereto. Dedicated docking station 123 coupled to docking station 125a is shown having a wireless connection to LMIS 104 via network 100. The handheld device 102 can be coupled to a plurality of beacons 126 having, each capable of a wireless information broadcast 128 to one of the portable handheld devices 102. A beacon 126 is stationed in the hospital emergency department, beacons 126 of the same or different type can be positioned throughout the emergency department, or broadly throughout the hospital. In an embodiment of the present invention, beacons 126 are Bluetooth devices, which broadcast device information on request, including, for example, address and device name. The device information broadcast 128 is received by the handheld device 102 and device information 130 is communicated by the handheld device 102 across the network 100 to the LMIS 114 or by some other wireless or wired network. Information can be sent between the portable handheld device 102 and the LMIS 104, although this would normally take place over network 100, other modes of communicating this information can be used, such as communicating via the network 120 and a dedicated workstation 122. In this case, messages can be sent indirectly to the user via the docking station. Also, a handheld device can be controlled by LMIS 104.

LMIS 104 can be any of a variety of conventional computing devices, such as a workstation computer. As will be apparent to one skilled in the art, it may be selected based on speed, memory capacity, and other performance characteristics necessary for providing the communications and data handling functions described herein. LMIS 104 is depicted as a single device. LMIS 104 can include a processor, memory, software, and a database. Data are stored in a conventional storage media (not shown) coupled to LMIS 104. It should be understood, however, that LMIS 104 may be implemented as a plurality of separate servers connected together over a network. Also, database 40 may include multiple databases (each containing a different type or amount of information). Databases 110 and 108 can further be distributed databases, having portions stored in a plurality of different locations or can be stored all in one location. For simplicity, LMIS 104 is referred to herein as a single, central server.

Network 100 and network 120 can be implemented as a single network (indicated in FIG. 1) that is wired, wireless, or a combination of wired and wireless. In one embodiment of the invention, network 120 is a wired network, such as a conventional wired Ethernet. Accordingly, dedicated docking workstation's 122 and ports for handheld devices 124a and 124b are coupled to network 120 using conventional wire technologies. In such an embodiment, network 100 is a wireless communication network using any type of wireless communication technology, for example, IEEE 802.11 technology. As such, network 100 includes a plurality of conventional access points (not shown) positioned at various locations throughout the facility such as in patient rooms, hallways, or other locations. As is well known in the art, the spacing between such access points should be such that wireless devices in communication with network 100 will always be within range of an access point, thereby providing complete coverage of the facility or a section of the facility. Network 100 is in communication with LMIS 104 via routers which process communications between network 100, network 104 and LMIS 104 according to principles that are well known in the art.

Portable handheld device 102 may include any of a variety of conventional portable computing and communication devices including "smartphones," pocket PCs, mobile PCs, Blackberries, Iphones, and Enterprise Data Assistants (EDAs). Portable handheld device 102 includes wireless functionality for communications over network 100. Accordingly, portable handheld device 102 includes a transceiver module, a microphone, and a speaker (none shown). Suitable devices include Motorola MC55, Intermec CN3, Samsung Omnia II, Apple iPhone. Portable handheld device 102 further includes a display, and a transceiver for communicating with Bluetooth mobile devices. In addition, memory, a camera, an RFID interface, or bar code technology (or other suitable technology), and input device and other networking controllers can also be used. Preferably, the portable handheld device 102 should be rugged to withstand drops and water resistant to withstand splashes from fluids.

Dedicated docking workstation's 122 can be workstations that include any suitable type of computing device having sufficient performance characteristics to function as described herein. In one embodiment of the invention, dedicated docking workstation's 122 are located at fixed locations throughout the emergency department. For example, dedicated docking workstation's 122 may be located in an admissions area, at nurse stations, hallway kiosks, and in patient rooms, etc. Dedicated docking stations 122 can also be placed on mobile carts ("Computer on Wheels" or COWS). Some or all of dedicated docking workstation's 122 can be coupled to ports for handheld devices 124a and 124 b and may have software running thereon capable of controlling the dedicated docking workstation's 122 and/or the ports for handheld devices 124a and 124b. Dedicated docking workstation's 122 may also be configured to function as an entertainment center for patients within viewing location of the dedicated docking workstation's 122. This entertainment function can be configured to utilize a minimum of the capabilities of the dedicated docking workstation's 122 and may include routing television programming to televisions in patient rooms, with the option of overlaying patient-oriented reminders, updates on the television screen as well as workstation monitor. The entertainment functionality can be configured to activate only when the dedicated docking workstation's 122 are not required for use according to the present invention. In another embodiment, ports 124a and 124b are coupled to a patient entertainment center and can override the programming directly; thereby placing the display of the handheld device on a display of the patient entertainment center.

In order to communicate to a LMIS 104, a portable handheld device 102 includes a transceiver and controller (not shown) which must communicate to the LMIS 104 via the wireless network 100. The communication involves an exchange of request and response messages between the portable handheld device 102 and the LMIS 104. The messages are sent from the portable handheld device 102 to the LMIS 104 and, likewise, messages are sent from the LMIS 104 to the portable handheld device 102.

Figure 2:
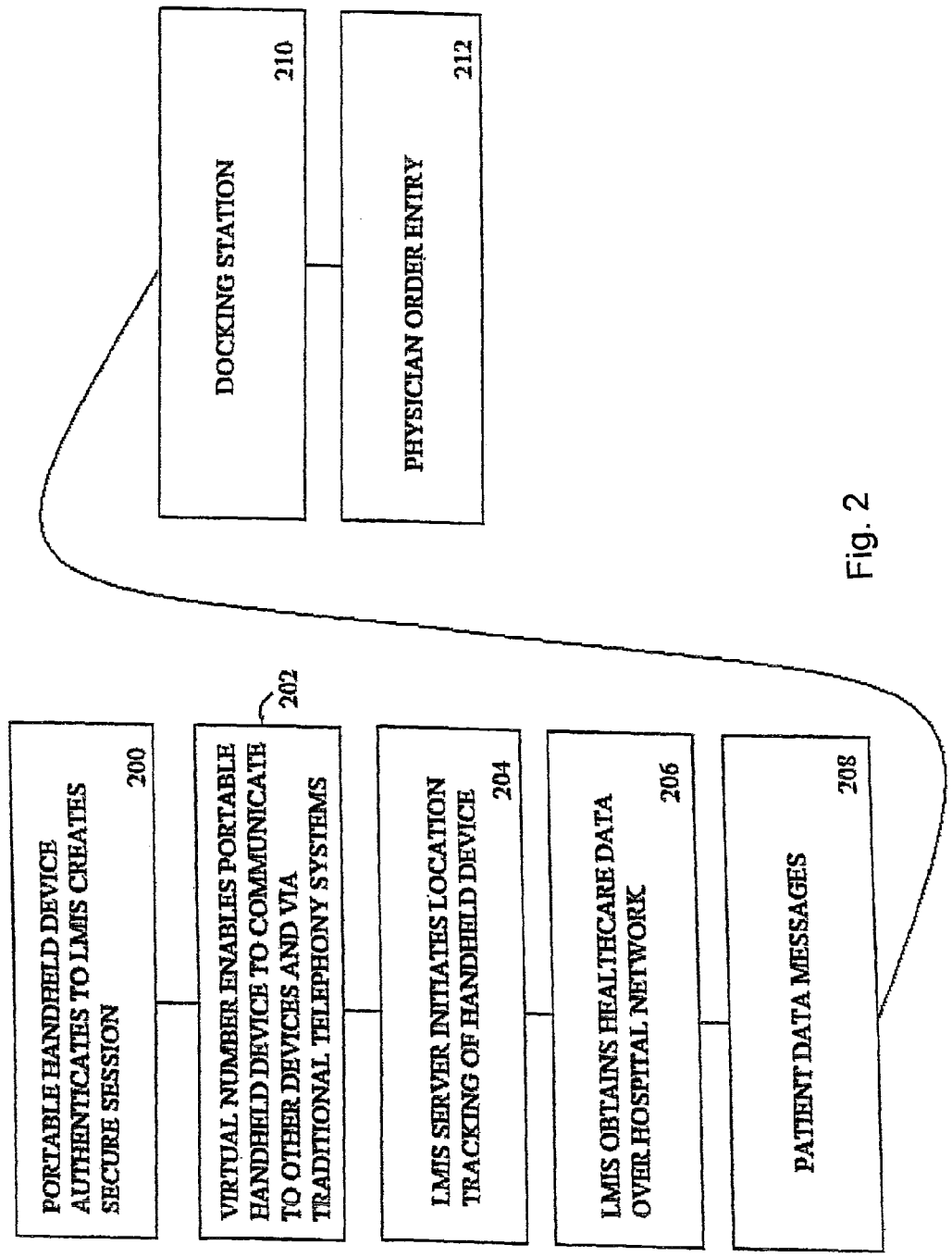
FIG. 2 is a flow chart of exemplary features of the portable handheld device in accordance with the present invention.

FIG. 2 presents an overview of the operations of software configured on a portable handheld device 102 according to the present invention in an embodiment suitable for an emergency department of a hospital. As seen in FIG. 2, the portable handheld device 102 can authenticate to an LMIS 104 to create a secure session (at step 200). Request and response messages are transmitted between the portable handheld device 102 and the LMIS 104. The messages, during the authentication process, include an authentication request message which is a set of user credentials passed from the portable handheld device 102 to the LMIS 104. If the LMIS 104 determines that the user credentials are valid, the authentication request can be further tested and then if valid, a validating response is sent to the portable handheld device 102 and information is stored on the server denoting a valid session between the particular portable handheld device 102.

The LMIS 104 can track which devices are currently authenticated in a table stored in memory on the LMIS 104, having an index of users and their status. The table associates a user to a portable handheld device 102, using the user identifier, user name, and a number associated to the portable handheld device 102. The type of information stored can include the user name, the machine identification number, the Internet address, the machine address, or any combination therebetween capable of at least uniquely identifying the session. In an embodiment of the present invention, the machine number is the network address of the portable handheld device 102 as associated with the network 100; however, one skilled in the art may use other identifiers, such as machine address.

The LMIS 104 can also include programming logic to determine whether a session is suspicious. For example, programming logic can be used to test certain aspects of the authentication. If a session fails the test, the LMIS 104 can be configured to lock down the portable handheld device 102, erase all information on the portable handheld device 102, and close the session, essentially disabling the device from further activity with the LMIS 104 and ED network 120. Programming logic can include various types of abnormal conditions which indicate suspicious actions. Conditions could include an incorrect machine ID, a machine ID that does not match the phone number and user name, or nonconforming network address. In addition, messages can be tracked to make sure that the timing and number of the messages is correct. Once the user is authenticated, the messages can be configured to transmit on a schedule, scheduled messages are an indication to the LMIS 104 that the phone is within the working area of the LMIS 104. If messages are not received, the portable handheld device 102 can be disabled.

The portable handheld device 102 having voice-over IP (VoIP), can be dynamically configured with a virtual phone number in order to communicate with other devices of the same type and also through traditional telephony services via the PBX 116, (at step 202). The portable handheld device 102 is assigned device information, which includes a virtual phone number, a device identifier and a user identifier. The device information is stored in a telephone directory database. If a telephone call is made from the portable handheld device to another device or an external telephone device, the portable handheld device transmits the virtual phone number or other device information. An external telephone device can directly call the portable handheld device by dialing the virtual telephone number for the portable handheld device. Upon dialing, the telephone call is routed through the network to the portable handheld device having said virtual telephone number.

The portable device 102 can also include a tracking feature (at step 204), whereby the LMIS 104 can initiate location tracking of the portable handheld device 102 with respect to proximate beacons 126. The LMIS 104 can obtain patient information and medical data (at step 206) over the hospital network 106 for display thereon in patient information screens. Patient medical data messages are transmitted to and from the portable handheld devices 102 (at step 208) from the LMIS 104 and then sorted and routed onto either the ED network 120 or the hospital network 106 and handled by the LMIS 104 in accordance with the present invention. Ports for handheld devices 124a and 124b can be provided to dock the portable handheld device 102 and thereby provide extra display and processing capacity for images which are not easily viewed on the portable handheld device 102, such as X-rays, blood pressure measurements, scans, and ECG's (at step 210). By communicating with the dedicated docking workstation 122 through ports for handheld devices 124a and 124b, the device can enable images and information to be sent from the portable handheld device 102 to the dedicated docking workstation display apparatus 122. At step 212, the portable handheld device 102 can be configured as a physician order entry system.

Figure 3:
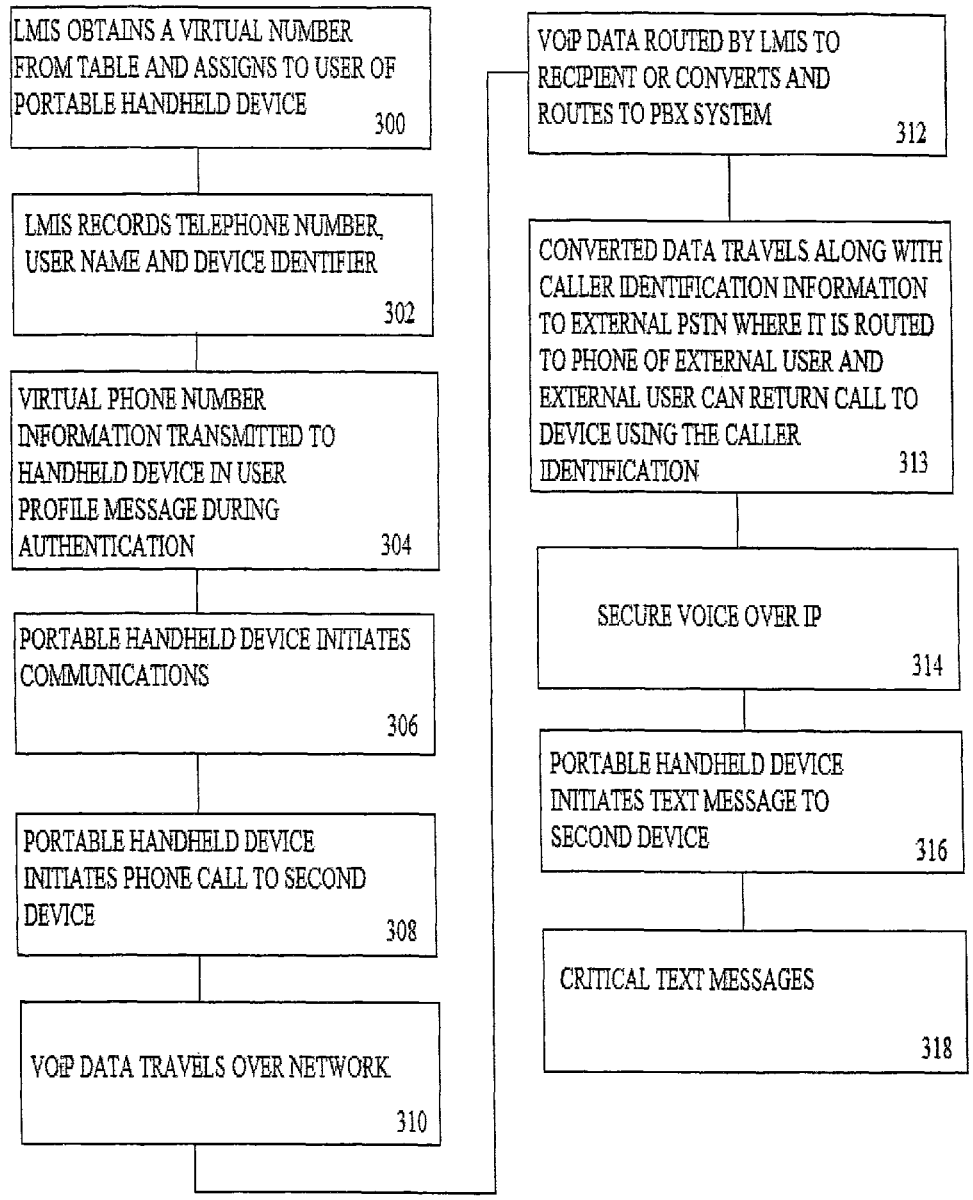
FIG. 3 is a flow chart of an exemplary interaction configuring the handheld device for telephone systems in accordance with the present invention.

FIG. 3 shows the steps after the portable handheld device 102 has been authenticated to the LMIS 104 over wireless network 100. The LMIS 104 first obtains a virtual number to assign to the device (at step 300). First, a pool of phone extension numbers is assigned to the LMIS 104 by the hospital PBX 116; these numbers are then managed by the LMIS 104. For example, the PBX 116 can assign a pool of numbers from 9000-9999 to the LMIS 104. These numbers can be allocated by the PBX 116 to the LMIS 104 and are not allocated again in the regular course of action by the PBX 116. The virtual phone numbers can be assigned to the handheld devices 102, as users authenticate, from this pool of phone numbers. For example, when a first user, Tom, authenticates, virtual number 9000 is assigned to Tom's handheld device 102 as the extension and stored in the LMIS 104 in a file with Tom's name and machine identifier. A second user, Scott, may authenticate and receive the next number in the pool, 9001. Later, when Tom returns his handheld device 102, the virtual phone number is transferred back to the pool of numbers and can be reallocated for a third user, David, when David's handheld device 102 is authenticated.

In another embodiment, the LMIS 104 can have program logic to reuse a previous virtual phone number, in this embodiment each time the device or the user is authenticated; the same virtual number is allocated. The LMIS 104 can manage a database of users and their phone numbers, each time a user logs on to a portable handheld device 102, the device would receive the number of the user. For example, from the original pool of numbers 9000-9999, a block of numbers can be used by the LMIS 104 for physicians. For example, 9000-9100 can be used for physicians. The remaining block, 9101-9999 is used for staff. For this embodiment, the LMIS 104 can then be configured to assign numbers permanently to physicians and have indication of the assignments stored persistently in memory on the LMIS 104 indicating the assignment of the number to the respective physicians, then each time a physician authenticates to the system the assigned number is allocated to the handheld device 102. For example, Tom authenticates a second time, this time the system checks a physician assignment table. Tom has been assigned virtual phone number 9001. The LMIS 104 allocates 9001 to Tom's authenticated portable handheld device 102. This is useful for situations where Tom has previously called an external physician, Claudia, and then Claudia would like to contact Tom later, after his first authenticated session has ended. Now, Claudia, having received phone calls from Tom previously, will know Tom's number because Tom's virtual phone number is captured by the caller identification of Claudia's phone system the same way that any POTS would identify caller numbers and enabling Claudia to call Tom anytime using this virtual number. If Claudia calls Tom back after his first authenticated session, if Tom has authenticated to the same handheld device 102, or another portable handheld device 102, he will have the same number and Claudia will reach him. In addiction, a physician could also be allocated a voice mailbox, the mailbox is then assigned to the phone number when the physician is not authenticated to a device, phone calls can be routed to the voice messaging system and stored in voice mail for the physician to recover from the system. Dynamically allocating the same number to a physician each time a session is created on any handheld device allows other users to communicate effectively with the physician, and other staff can immediately know if the number is a physician's by the block number. Under this method, the phone number would follow the user from device to device each time the user authenticates to a new device.

It is also possible to allocate a number based on position assignments, for example, a particular station can be assigned a number. In this embodiment, when the user logs on, they would also be required to convey status information, such as which nurses station assignment they have received or staff type, then the phone number would be given from the database according to previously assigned numbers to the particular position. According to the present invention, the phone number does not have to be permanent.

The LMIS 104 then records the telephone number, user name, and device identifier (at step 302). The device identifier can be the network address of the portable handheld device 102, or it can be a machine ID or any other identifier that uniquely identifies the portable handheld device 102 as this is not a limiting feature of the invention. The virtual phone number information is transmitted (at step 304) to the portable handheld device 102 in a user profile message. The user profile message is sent during the authentication session previously described. The profile messages, in addition to the authentication message, and the profile information is exchanged from the LMIS 104 to the portable handheld device 102 and programming logic on the device 102 can configure the phone to operate on VoIP with the virtual phone number. The portable handheld device 102 can then initiate communications to others (at step 306) because the phone is now configured to and activated to respond and transmit phone calls over the VoIP protocol using the wireless network 100 and LMIS 104 as a routing system for routing VoIP telephone communication. The portable handheld device 102 is then used to initiate phone calls with one another over the wireless network or to other phones on the PSTN 118 (at step 308) through the LMIS 104. Furthermore, the portable handheld device can receive telephone calls from the PSTN 118 if the external caller dials the virtual telephone number assigned to the portable handheld device. The user can dial a number directly, find other virtual phone numbers in the network 100 or search by name for authenticated users. Voice-over-Internet data travels over the network 100 (at step 310) and is routed by the LMIS 104 (at step 312) to the recipient portable handheld device 102 or it is communicated to the PBX system 116 and then outward to the PSTN 118. Telephone calls to the PSTN 118 are routed along with their virtual phone number, which will indicate in caller identification to external callers the allocated virtual phone number of the user (at step 313). In this way, the phone number is communicated to external users and the external users can call the portable handheld device 102 using the information. External users who dial the virtual number will have their calls routed through the PSTN and/or PBX to the LMIS server. The telephone call by the external user will be routed to the portable handheld corresponding to the assigned virtual telephone number. If the telephone message includes information, such as a virtual phone number, that indicates to the PBX 116 that the phone call belongs to a user of a portable handheld device 102, then that packet is routed to LMIS 104 for handling. This information is secure over the Emergency Department and possibly hospital network (at step 314).

The portable handheld device 102 can also initiate text messaging (at step 316) to other devices 102. Handheld device 102 is configured to send robust critical text messages (at step 318). A critical text message includes handling information in addition to having a body which can be text, picture, audio, attached file, documents, database, spreadsheet, or other information known in the art. The handling information indicated to a second handheld device 102, that a message includes critical material and acknowledgement is required. The user receives the message and must acknowledge that the message has been reviewed and received. This improves communication reliability and accountability in the ED by assisting physicians, nurses, and other staff with reminders and also enforcing policy by enabling tracking of messages and timestamps. If the message is not acknowledged, then the system can be configured to respond back to the originating device in a timely fashion notifying the originating device 102 and user that the message has not been received and that they should take further action. For example, if Tom was trying to notify Scott of urgent information concerning one of Scott's patients that required immediate action, Scott's portable handheld device 102 would alert Scott of the message and Scott could take action. If Scott is unable to act on Tom's message (for instance, Scott is delivering a baby and has both hands occupied), Tom's device would remind Tom after a set period, for example, one minute, that Scott has not received the urgent message. Tom could then take further action, for instance, querying Scott's location or contacting the charge nurse. Alerts can be implemented by delivering a signal, a unique ring, a distinct sound, vibration, a text box on the device, or other warnings known in the art sufficient to alarm the user.

Figure 4:
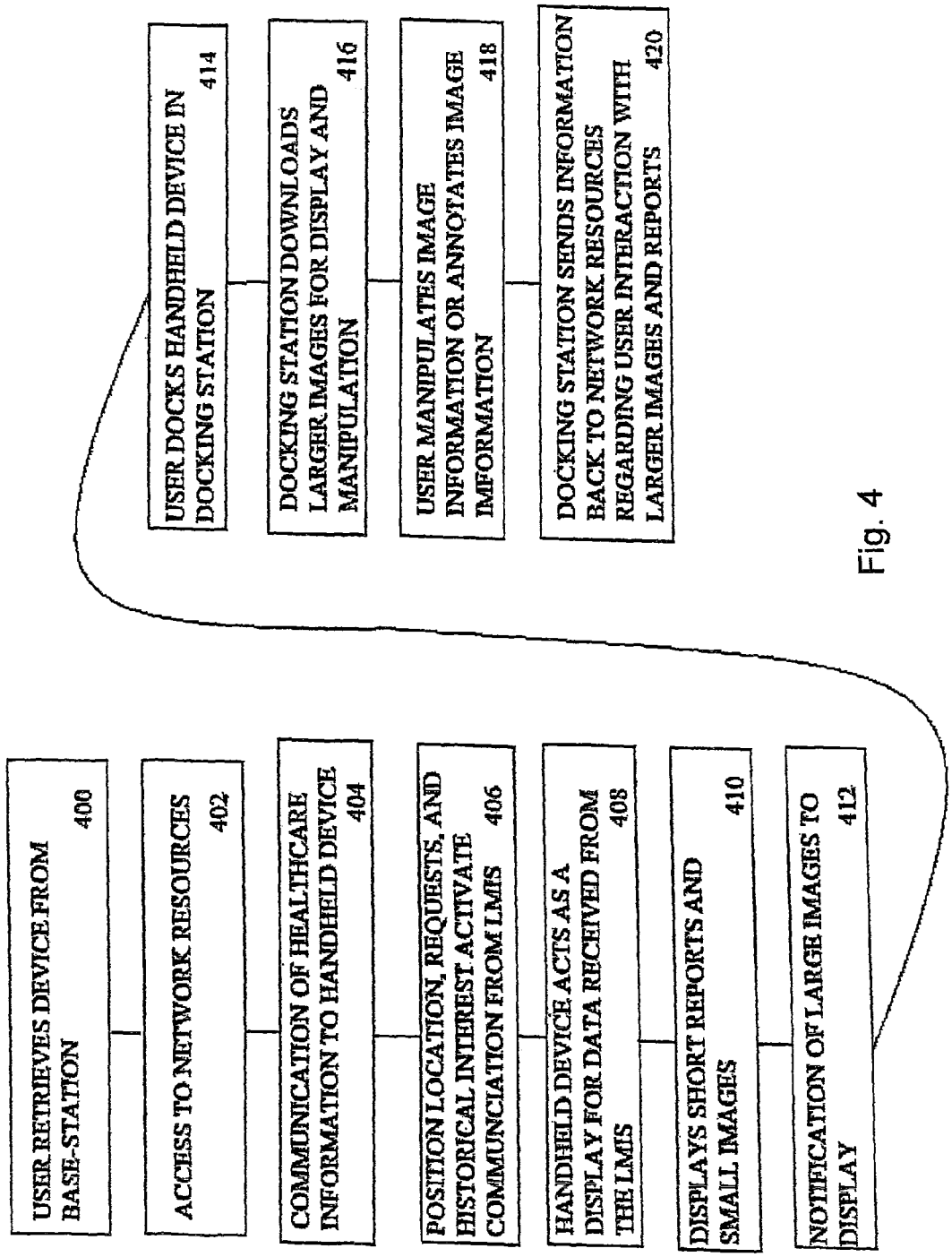
FIG. 4 is a flow chart of an exemplary interaction configuring the handheld device as a point-of-care system in accordance with the present invention.

With reference to FIG. 4, as seen at step 400, when a user wishes to use ports for handheld devices 124a and 124b, the portable handheld device 102 is first taken from the bay station, where it is charged and waiting for a user (at step 400). User authenticates and accesses network 100 and network 120 resources (at step 402). Medical information is transmitted to the portable handheld device 102 from the LMIS 104. The LMIS 104 access databases 108 and 110 for information or from other messaging systems. The LMIS 104 transmits information to the portable handheld device 102 (at step 404). In normal operation, the device 102 sends position location messages, request messages and historical interest tracking messages which can activate further communication from the LMIS 104 (at step 406). The portable handheld device 102 having a display and patient information screens then acts as a display for data messages received from the LMIS 104 (at step 408). The patient information screens on the portable handheld device 102 can display short reports and small images (at step 410). For large images, the handheld device 102 can be notified of their existence on the LMIS 104 but not sent to the device 102 (at step 412). A user can then activate ports for handheld devices 124*a* and 124*b* in the hospital by placement of the portable handheld device 102 to form a couple with the ports for handheld devices 124*a* and 124*b*. The coupling transfers the session of the device 102 to the dedicated docking workstation 122 (at step 414). Once the docking station 122 is coupled to the portable handheld device 102, the dedicated docking workstation 122 can download larger images from the LMIS 104 to the dedicated docking workstation 122 for display and manipulation on a large screen. The user can also work with different input devices, such as a normal size keyboard, printer, scanner that can be attached and configured to work with the dedicated docking workstation (at step 416). The user then manipulates the information or annotates image information (at step 418). The docking station 122 then sends information back to network resources regarding user interaction and this information is automatically stored on the LMIS 104 as part of the authenticated users session state (at step 420).

Dedicated docking workstation 122 can be configured to stream content to patient entertainment center 134 in the form of ED evaluation information, prognosis, or educational material, in order to save time and reduce medical error. The television signal can be superimposed with content by the docking station, such as text box or progress bar. This content can be routed (manually or automatically) based on a nurse's location to the docking station from other points in the hospital using patient information and tracking information. The portable handheld device 102 can keep track of patient's location and can forward this information to a docking station located near patients based on a bar code of the patient's identification. The center 134 can then display scrolling next for examples showing information for a patient, such as how many labs are competed, reminders of medicine, where the labs are, and what steps are still pending in the ED procedure for a patient. This can be, for example, in the content of a scrolling box on the television.

If a physician docks the portable handheld device 102 in ports for handheld devices 124*a* and 124*b*, the physician can override the television signal and thereby control the entertainment center 136. The physician can then share patient information screens, such as X-rays or charts, from the portable handheld device 102. A patient or family could review the content without moving from a location.

Figure 5:
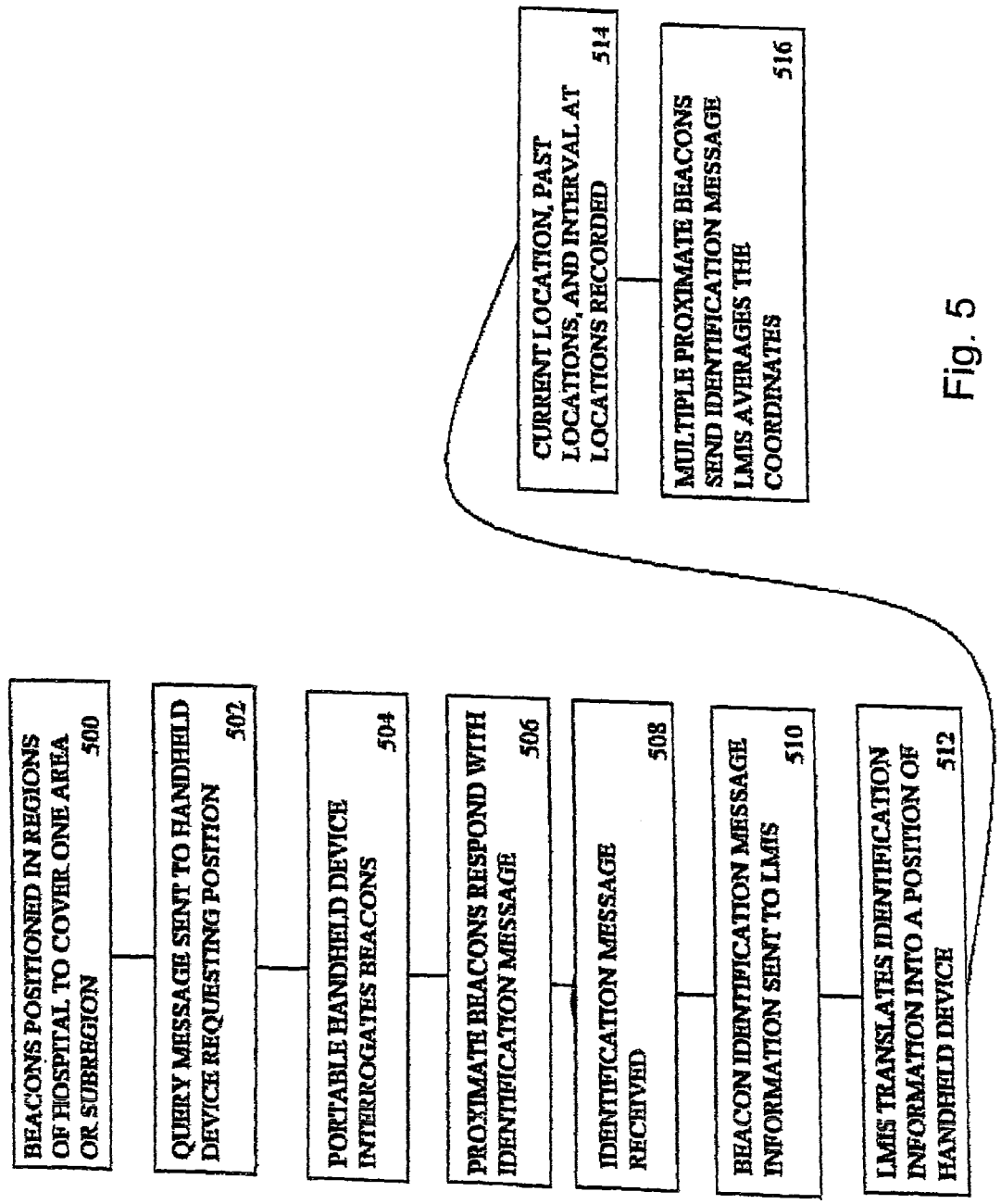
FIG. 5 is a flow chart of an exemplary positioning system in accordance with the present invention.

The portable handheld device 102 can also automatically report position information to the LMIS 104 based on proximate location to beacons 126. As seen in FIG. 5, at step 500 beacons 126 are positioned in regions of the hospital to cover an area or subregion. A query sent by the LMIS 104 to the portable handheld device 102 requesting position activates programming logic of the device 102 (at step 502). The portable handheld device 102 then interrogates any proximate beacons 126 (at step 504). When the interrogation takes place, the proximate beacons respond (at step 506) with device information broadcasts 128. These broadcasts 128 include identification information for the particular beacon 126 which can be captured by the handheld device 102. When the portable handheld device 102 receives the wireless broadcasts 128 (at step 508), the proximate location of the device can be calculated by matching the machine name to a machine name map address in a database. The interrogation can take place multiple times and there can be multiple devices interrogating the portable handheld device 102 at one time. The beacon identification information from broadcast 128 can be sent back to the LMIS 104 (at step 510). The LMIS 104 translates the identification information into a position of the portable handheld device 102 using a name map address in a database (at step 512). The current location, past location, and intervals at locations for a device 102 can be recorded (at step 514). Placement of beacons 126 can sometimes cause multiple proximate beacons 126 to respond with broadcasts 128 of identification messages (at step 516). If multiple broadcasts 128 are received, the LMIS 104 averages the coordinates of all the beacons 126 as the proximate location of the portable handheld device 102.

Figure 6:
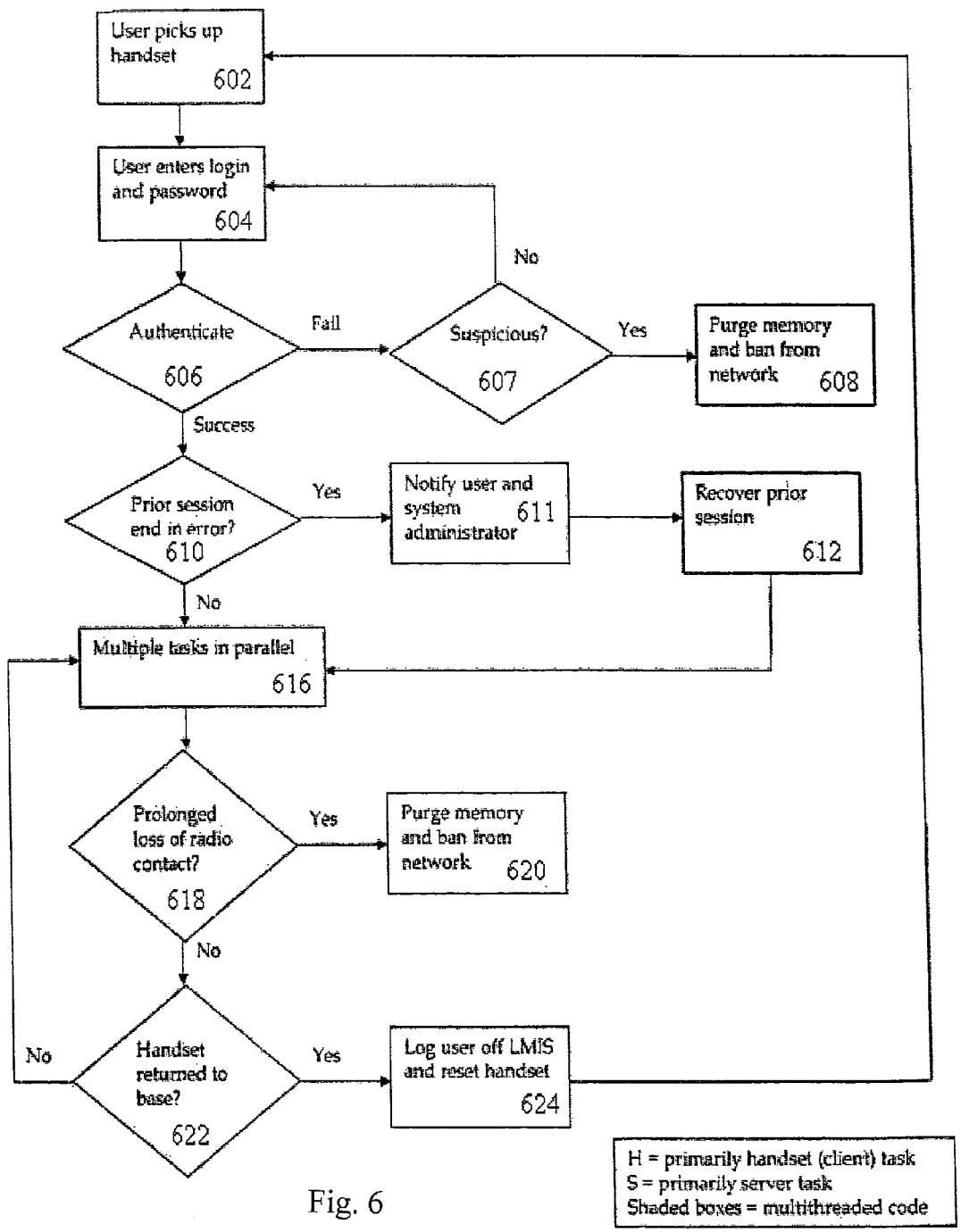
FIG. 6 is a flow chart of the portable handheld device authentication process in accordance with the present invention.
Figure 7:
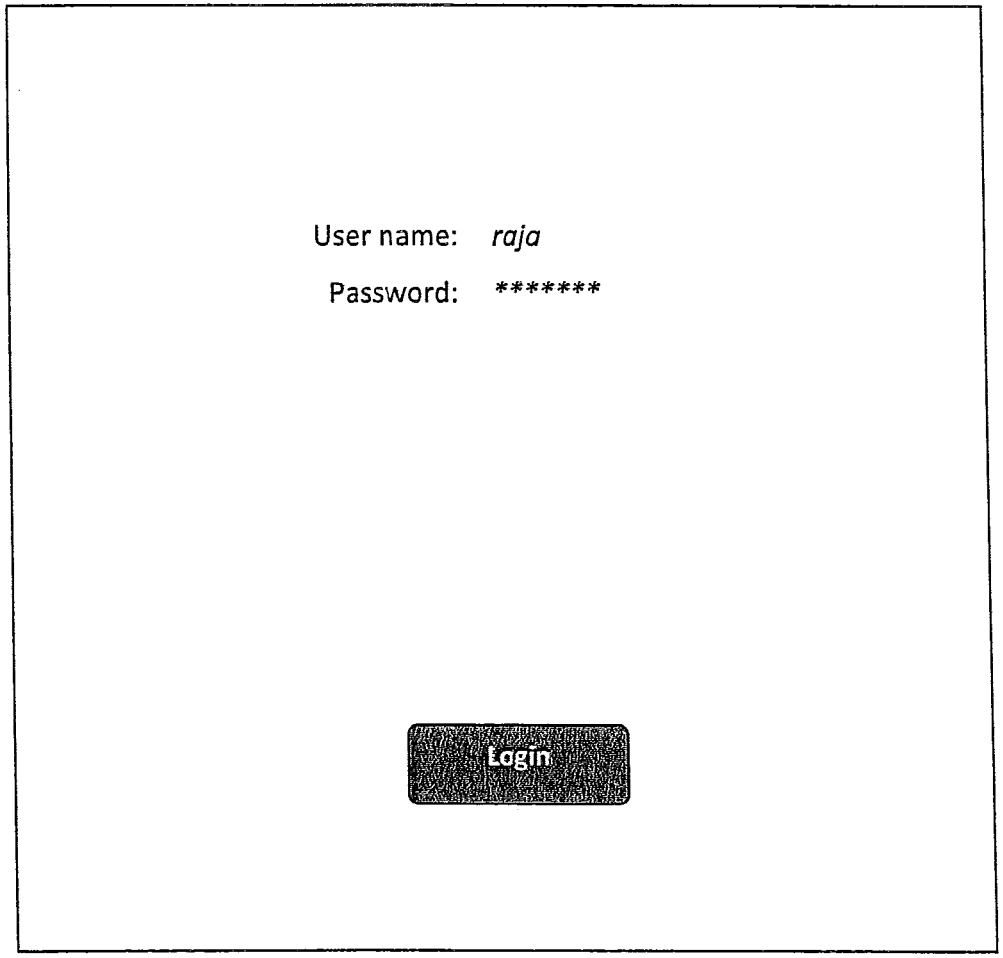
FIGS. 7-12 are screen shots generated information management software, operated by a portable handheld device in accordance with the present invention.

With reference to FIG. 6, at block 602, a method of using the present invention begins when a user picks up the portable handheld device 102. A user can authenticate to the LMIS 104 at block 604, preferably by entering a user identification code and a password via the portable handheld device 102. FIG. 7 is an example of an authentication screen. The authentication screen includes a field for entering the user name and a field for entering password information. A login button can initiate the authentication session.

If the LMIS 104 determines, based on previously entered information stored in the system, that a valid user identification code has been entered, and that the proper password of that user identification code has been entered, and further that the device has not been compromised in any way, access to further features of the system is allowed. At block 606, authentication takes place. If authentication fails, conditional program logic is used to determine if the authentication is a suspicious authentication at block 607, such as too many attempts, different user names, or inconsistent addresses or machine numbers. If authentication is determined to be suspicious by LMIS 104, the memory of the handheld device 102 is immediately purged and the portable handheld device 102 is banned from the network 100 at block 608. Otherwise, if not a suspicious authentication, the program returns back to block 602 and the user is presented the authentication screen again and enters login identification and password.

Returning to block 606, if authentication is successful, in decision block 610, LMIS 104 determines if the prior session for device 102 ended in error. If the previous session did end in error, the user and a system administrator is notified at block 611 in order to ensure that the error can be investigated. The prior session state is then recovered by the LMIS 104 and restored to the device 102 at block 612. It should be understood that other security measures known in the art could be implemented, such as requiring the user to point and click on a list of users that are granted access to the system and then filling in authentication information.

Figure 8:
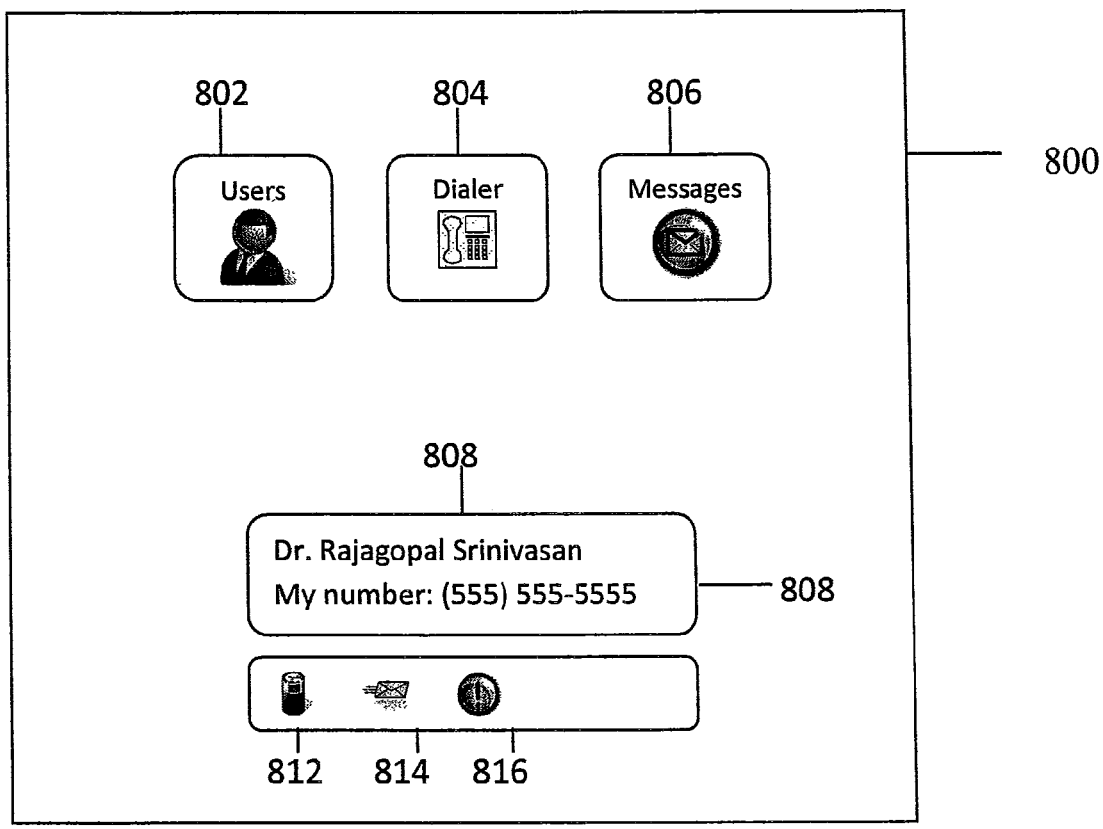

After successfully authenticating, at block 616 the user is presented with the medical information systems home screen 800 as shown in FIG. 8 and can proceed to use the device 102. Home screen 800 includes a users tab 802, a dialer tab 804, and a messages tab 806. Home screen 800 includes user information display box 808, which displays the name of the current user, Dr. Rajagopal Srinivasan and the virtual phone number that is allocated to him. Further information is shown in the status bar 810, including the power indicator 812, message indicator 814, and critical text indicator 816.

Figure 9:
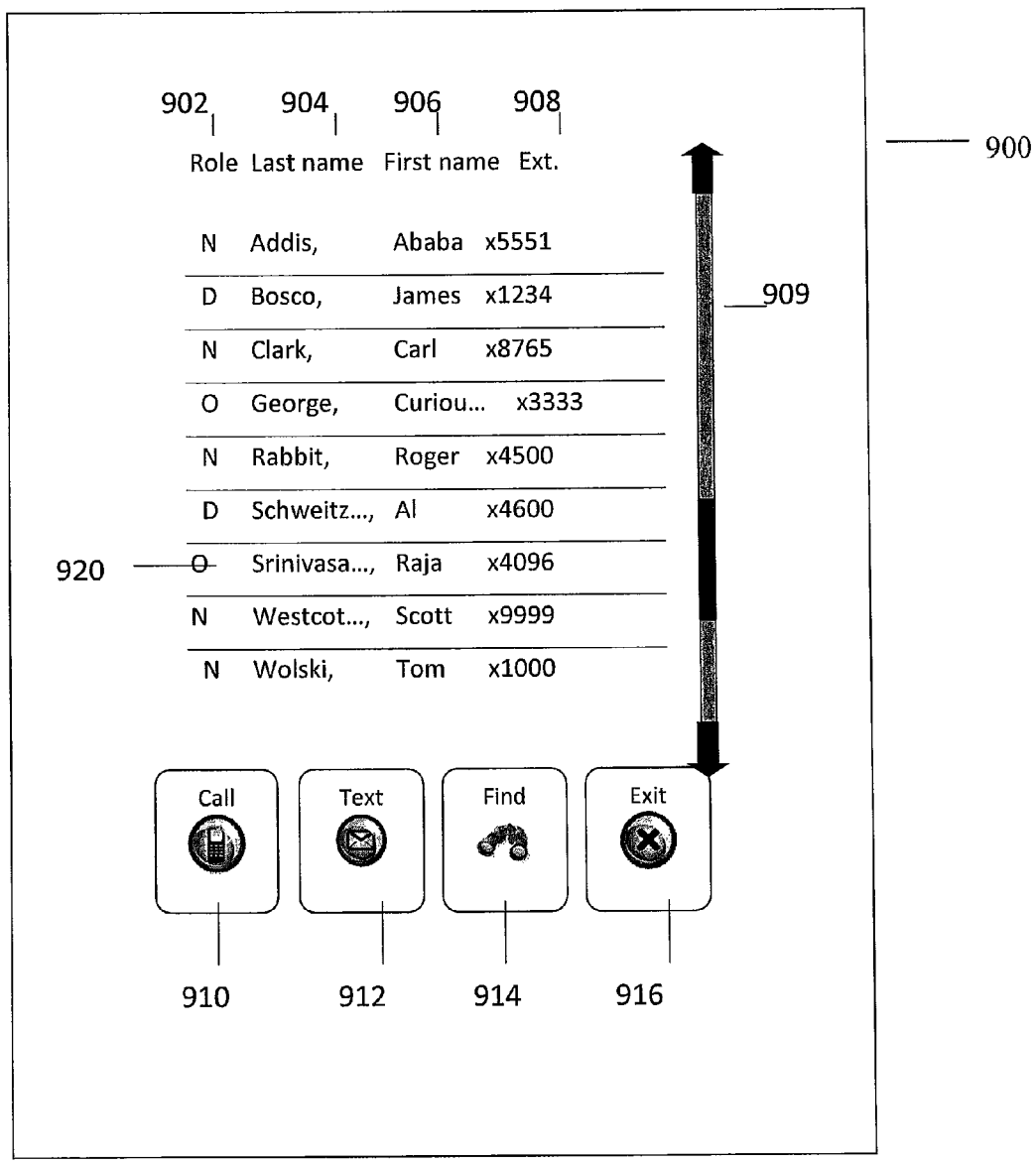

If the users tab 802 is selected, the system proceeds to a user screen 900 which is shown in FIG. 9. In the user's screen 900, a handheld device user list includes the role 902, first name 904, last name 906, extension 908, and scroll bar 909. The user list includes all names of users currently authenticated to the LMIS 104. In user's screen 900, there are a number of users logged onto the network. The scroll bar 909 provides a mechanism to scroll through the list. The list can be automatically updated by the LMIS, scheduled or manually refreshed. The user screen 900 also includes a number of actions that a handheld user can take including a call action 910, a text action 914, a find action 916, and an exit action 918. These actions will perform a function on the portable handheld device 102. For example, in FIG. 9, a user has selected Rajagopal Srinivasan at extension 4096, shown by the highlighted area around row 920. If the user clicks the call action 910, a phone call will be placed to the highlighted user's extension in accordance with the steps outlined previously for calling another portable handheld device 102. Selecting the text button 914 places a critical text message to the portable handheld device 102 of Dr. Srinivasan. The find action 916, if selected, can query another user's portable handheld device 102 of visible beacons 126 to estimate location within the ED.

Figure 10:
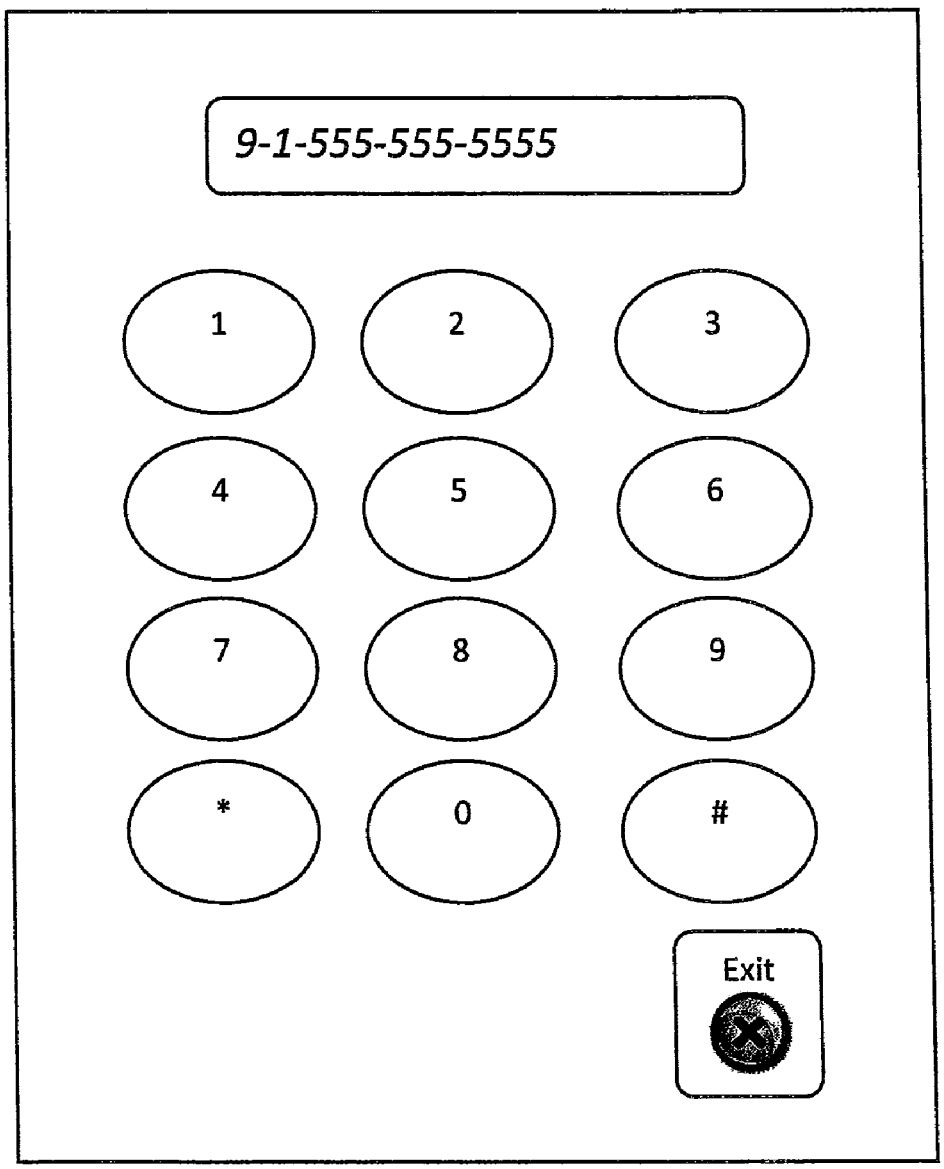

Returning to FIG. 8, if dialer 804 is selected, the system proceeds to FIG. 10 where a user can dial a telephone number of either another portable handheld device 102 or a number outside the network 100. The user can dial another party using the number keypad.

Figure 11:
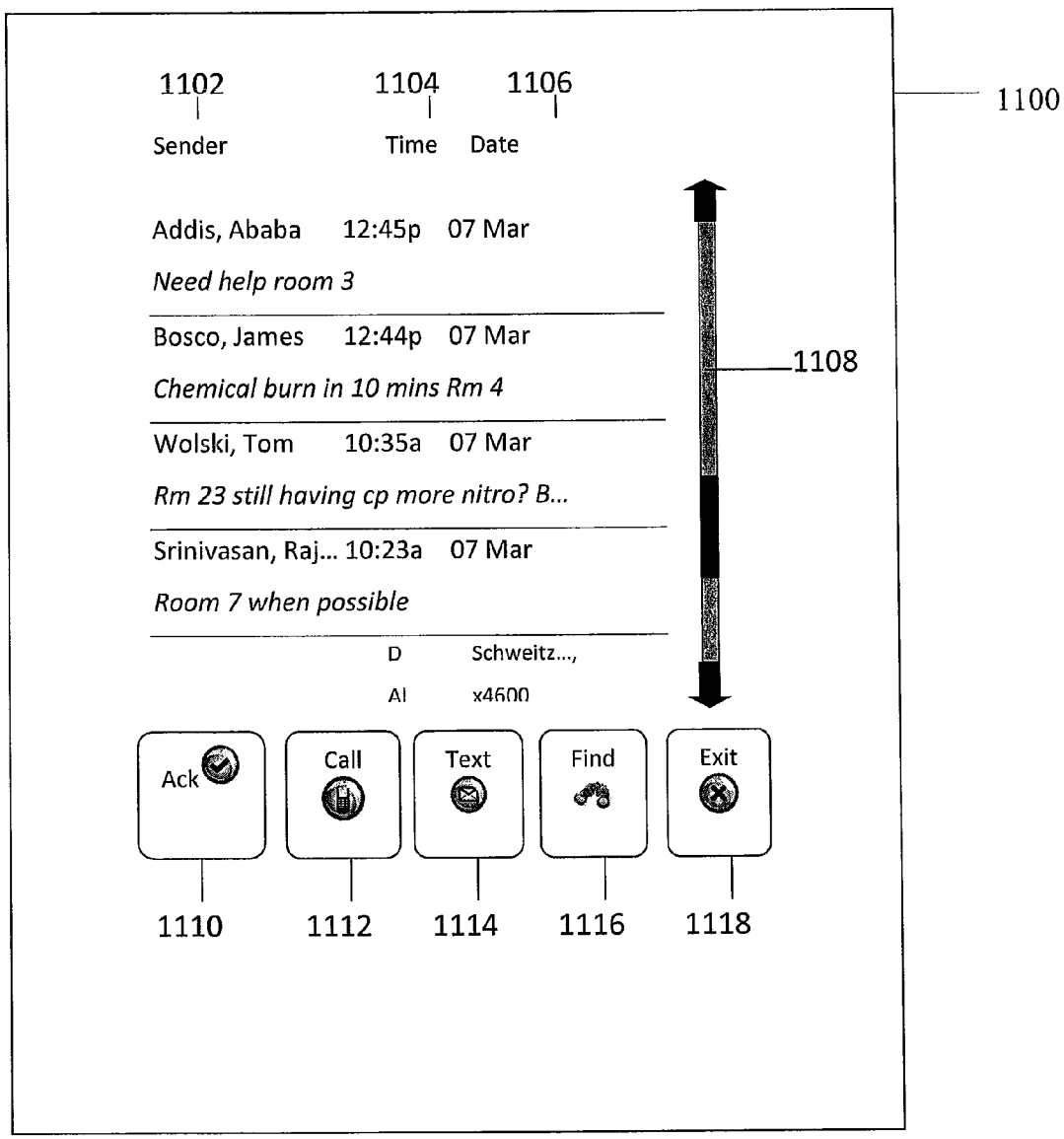

Returning again to FIG. 8, if the messages tab 806 is selected, the system proceeds to a message screen 1100 which is shown in FIG. 11. In the messages screen 1100, a handheld device message list includes the sender 1102, time 1104, date 1106, and scroll bar 1108. The message list includes all messages of the user currently authenticated to the LMIS 104 on the device 102. In messages screen 1100 as shown, there are a number of messages listed for the current user. For example, a message stating "need help in Room 3" was sent by Ababa Addis on March 7 at 12:45 p.m. Also, Tom Wolski has sent a message, highlighted as shown, that states "labs back RM 23 positive troponin . . . " The user can select the message to expand it on the screen of the portable handheld device 102. The scroll bar 1108 provides a mechanism to scroll through the list. The list can be automatically updated by the LMIS 104, scheduled or manually refreshed. The messages screen 1100 also includes a number of actions that a handheld user can take including acknowledgement action 1110, call action 1112, text action 1114, find action 1116, and exit action 1118. The find action 1116, if selected, can query another user's portable handheld device 102 of visible beacons 126 to estimate location within the ED. The acknowledgement action 1110 must be selected when a text message has been received in order to send an acknowledgement message back to the sender and complete a security handshake and indicating to the sender that the message has been read. The call action 1112 will activate the telephone dialing to call the selected sender of the selected message. For example, seen in FIG. 11, if the call action 1112 is clicked, a call will be placed to the extension of Tom Wolski as highlighted if he is still authenticated to his portable handheld device 102.

When a user selects the text action 1114, the system proceeds to a compose screen. The compose screen includes a message. The message includes text which will be appended to the message body. After the message has been created, the user has the option to send the message or can still call, find, or cancel. The compose screen also includes a number of actions that a handheld user can take including send action, call action, find action, and cancel action. When the user has finished composing the message, selecting send action will initiate the critical text message process. The find action, if selected, can query another user's portable handheld device 102 of visible beacons 126 to estimate location within the ED.

Figure 12:
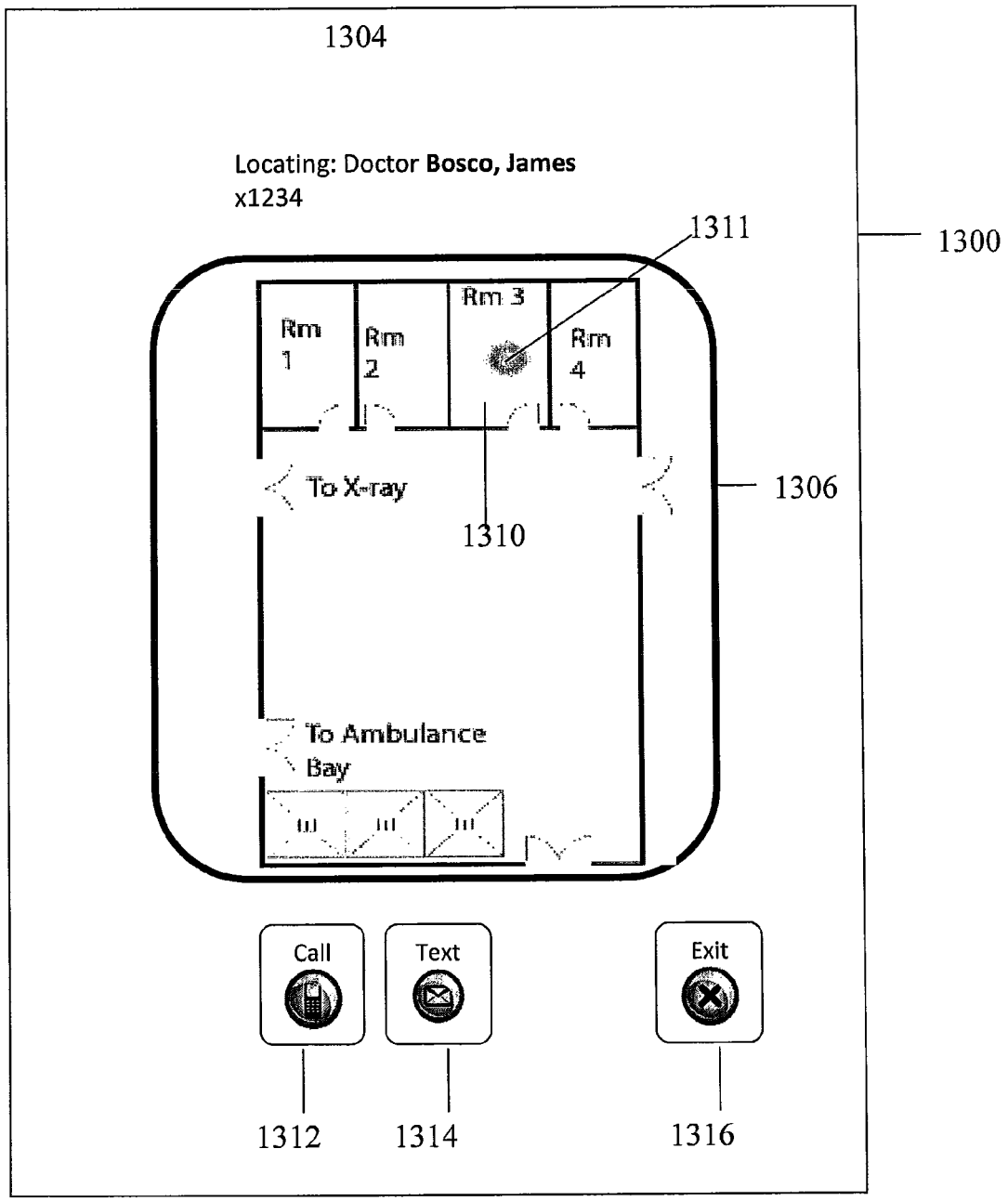

With reference to FIG. 12, when a user selects the find action 914, or find action 1114, from any of the screens 900, or 1100, the system proceeds to a locating screen 1300 configured for a hospital emergency room. A plurality of beacons 126 can be disposed in the various rooms and areas of the hospital emergency room. At some areas, multiple beacons can be used. Locations are recorded and stored for each of the beacons 121. Locations can be stored as coordinates, room numbers, areas, or any other mapping techniques. The location is stored in file linked data, an association of beacons, and location. Machine ID can be used to identify the beacon. From this information, and a map, users can be tracked around a hospital. When users of each handheld system authenticate their handheld device 102, they are identified in the system. As they move from room to room in the hospital their device can interact with the beacons arranged therein. The locating screen 1300 includes a map window 1306 and a locator window 1304. The map window 1306 provides a top perspective view of the rooms in the hospital. The locator window 1304 provides an identification of the personnel sought. After the find action 914 is selected, a transceiver of the handheld device sends a location message wirelessly to the LMIS. The LMIS then responds by sending an activation message to the device registered for the identified personnel. The activation message can be notification to a second handheld device to query location. When a handheld device is activated to query location, it senses surrounding beacons by listening for a signal from a beacon 126 located proximate to its current position. The beacon 126 can be configured to automatically broadcast an information signal or alternatively can be configured to respond only when directly interrogated. When the sensed beacon 126 is configured to respond to interrogation, the handheld device 102 can interrogate the sensed beacon 126 for a device information broadcast 128, the broadcast 128 is an information signal having device information 130, including device address, device name, or device type. When the broadcast is received by the handheld device 102 it is relayed to the LMIS 104. The LMIS 104 calculates position by matching the device information 130 to stored device information, including address and position tuples for each beacon 126 stored in a database or file. The LMIS 104 can then store and/or forward the device information 130 in association with the found handheld device 102 to the requesting handheld device 102. Alternatively, a handheld device 102 can be configured with stored device information capable of enabling individual handheld devices 102 to calculate position themselves, thereby forwarding a request directly to a searched device and then the search device forwarding information directly to a requesting device, bypassing the LMIS 104 and transmitting the position information directly between two handheld devices. When the handheld device 102 receives the location information from the LMIS 104, it can be rendered into a map showing a location indicator 1311 of the searched device 102, and therefore the sought personnel. As shown in FIG. 12, map window 1306 includes a number of rooms. Room 3 1310 has an indicator 1311 which can show the location of tracked personnel. The locating screen 1300 also includes a number of actions that a handheld user can take including call action 1312, test action 1314, and exit action 1316. Historical information can be stored in a file also, either on a device 102 or server 104. From historical information, movement around a hospital can be shown. Time stamps can also place a location into a time dimension.

Returning to FIG. 6, during the above-described tasks, there is continual tracking of contact between the LMIS 104 and the handheld device 102 for determining if a prolonged loss of radio contact occurs at block 618. If prolonged loss occurs, memory is purged and the device 102 is banned from the network at block 620. The portable handheld device 102 can be used until it is returned to the base at block 622. When the portable handheld device 102 is returned to the base at block 624, the user is logged off and the LMIS 104 resets the portable handheld device 102 and the next user can log on and use the portable handheld device 102 and it will start again at step 600 and the login process begins again at step 602.

Figure 13:
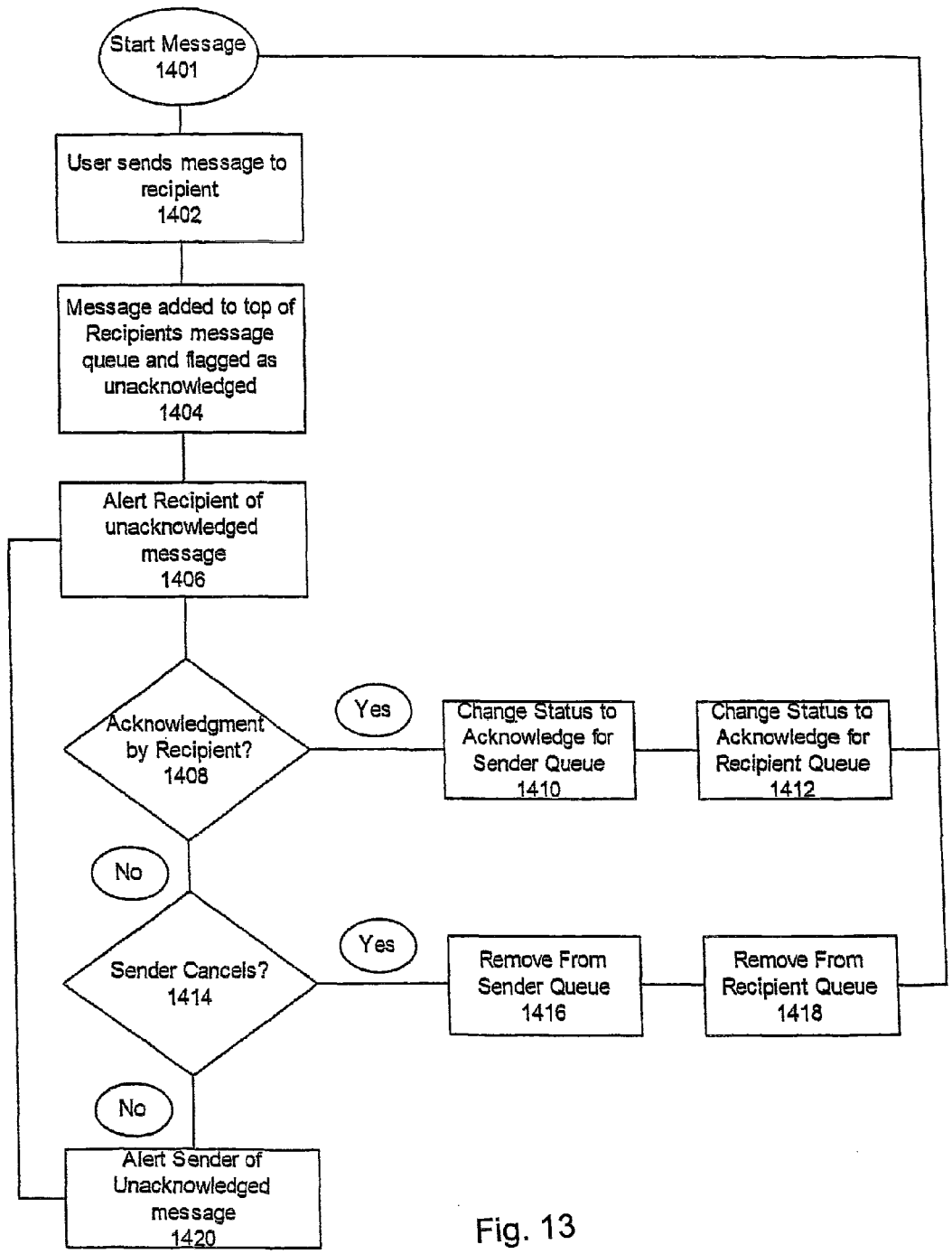
FIG. 13 is a flow chart of the portable handheld device reliable messaging protocol in accordance with the present invention.

A substantial portion of tasks performed by physicians and nurses involves the collection, storage, communication, and analysis of information. Medication lists, blood pressure, lab results, even the entry and execution of orders, are crucial bits of information that benefit from the present inventions reliable infrastructure. A time-critical task, such as reporting a critical lab result requires the urgent transmission of information from lab to nurse to physician in many EDs. This almost always needs to be followed by some acknowledgement from nurse and physician that the information was reviewed. To protect each agent in this highly unreliable chain, documentation of receipt is usually made by the transmitting agent, which of course becomes suspect after an adverse outcome occurs and the physician involved denies knowledge of the critical value. With reference to FIG. 13, at block 1401, a method of using the present invention to send a secure message begins when a user starts by creating a message.

An example of a message a physician may send to another physician scan include text which will be appended to a message body. After the message has been created, the user scan send the message to a recipient at block 1402. Alternatively, before sending the user still has the option to call the recipient, find recipient and go to the location, or cancel the message. At block 1404, the message is added to the top of the intended recipients message queue. The message is automatically flagged as unacknowledged. After the message arrives, an alert informs the recipient that the unacknowledged message exists at block 1406. Then the recipient must acknowledge the message, at decision block 1408. The handheld device 102 can determine if a message is acknowledged and if it is change the status for both the sender and the recipient. At block 1410, the status is changed for the sender of the message to show that it has been acknowledged. At block 1412, the status is changed for the recipient of the message after the sender has verified that acknowledge was successful, to show that it has been acknowledged. In another embodiment, blocks 1410 and 1412 could be performed in parallel. Returning to block 1408, if the recipient fails to acknowledge within certain parameters, such as a timed duration, for example 15 seconds, the sender can cancel the message at decision block 1414. If the sender cancels the message, then in block 1416 the message is removed from the sender queue. Next, the cancelled message is removed from the recipient queue in block 1418. Returning to block 1414, if sender does not cancel the message, then the sender is alerted of an unacknowledged message at block 1420 and program logic returns to block 1406 to again alert the recipient of the unacknowledged message.

Figure 14:
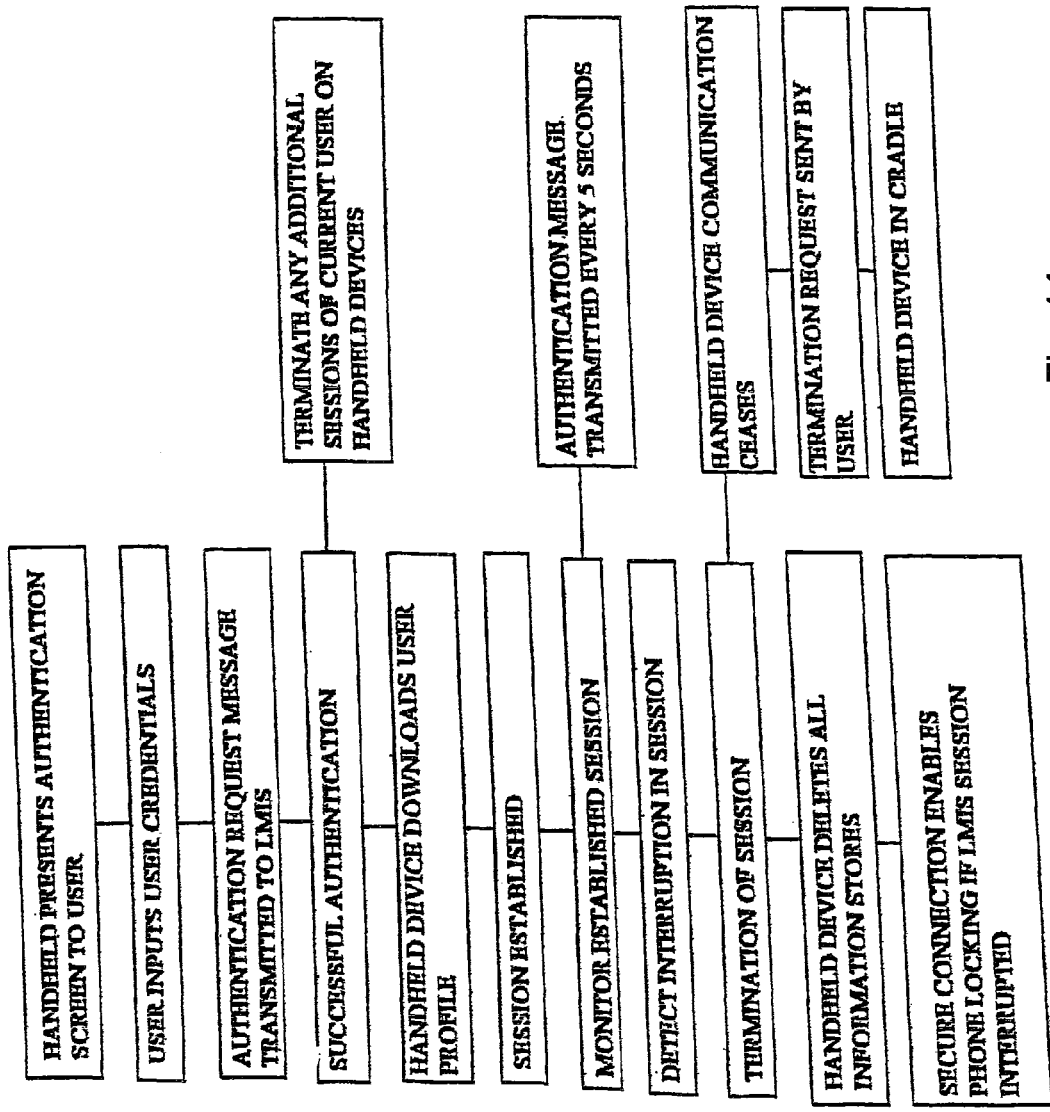
FIG. 14 is a flow chart of exemplary interactions of the present invention.

In FIG. 14, the interactions of the phone are shown, during authentication, a session, inactivation, and logoff.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

The invention claimed is:

1. A method of tracking and communicating with a hospital personnel comprising:
providing said hospital personnel with a portable handheld device comprising storage memory, a processor, an input device, a transceiver, and a display,
authenticating said handheld device;
assigning said portable handheld device with a private branch exchange number;
linking said private branch exchange number to a name of said hospital personnel;
storing said private branch exchange number and said name linked to said private branch exchange number on a server in a database;
downloading said database to said portable handheld device;
identifying a location of said hospital personnel comprising interrogating a proximate location of said portable handheld device;
storing said location on said server;
generating patient information screens on the display, using patient information from at least one received message from the server;
connecting to a docking station attached to a host computer, whereby a session is transferred to the host computer so that the host computer can communicate directly with the server or can communicate with the server through the handheld and patient information is displayed on said host computer; and
processing to show the patient information on the host computer using at least one received message by the host computer from the server.

2. The method according to claim 1, further comprising displaying said database on said display of said portable handheld device.

3. The method according to claim 2, further comprising selecting said name of said hospital personnel linked to said private branch exchange number from said display.

4. The method according to claim 1, wherein said proximate location is determined by transmitting an interrogating signal from said portable handheld device to a beacon, sending a machine identification code from said beacon wherein said code identifies said beacon, and transmitting said code and a beacon location code from said device to said server.

5. The method according to claim 1, further comprising downloading said location of said hospital personnel.

6. The method according to claim 1, further comprising downloading patient information to said portable handheld device from said server or a second server.

7. The method according to claim 1, further comprising overriding a patient entertainment center.

* * * * *